(12) United States Patent
Bernhardt et al.

(10) Patent No.: US 7,860,288 B2
(45) Date of Patent: Dec. 28, 2010

(54) X-RAY DEVICE HAVING A DUAL ENERGY MODE AND METHOD TO ANALYZE PROJECTION IMAGES DETECTED IN THE DUAL ENERGY MODE

(75) Inventors: Philipp Bernhardt, Forchheim (DE); Estelle Camus, Mountain View, CA (US); Martin Hoheisel, Erlangen (DE); Thomas Redel, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 880 days.

(21) Appl. No.: 11/809,276

(22) Filed: May 31, 2007

(65) Prior Publication Data

US 2008/0044073 A1   Feb. 21, 2008

(30) Foreign Application Priority Data

May 31, 2006   (DE) .................. 10 2006 025 423

(51) Int. Cl.
*G06K 9/00* (2006.01)
*H05G 1/70* (2006.01)
*H05G 1/10* (2006.01)
*A61B 5/05* (2006.01)
*A61B 5/02* (2006.01)

(52) U.S. Cl. .................. 382/128; 378/92; 378/101; 600/425; 600/481

(58) Field of Classification Search .............. 382/128, 382/129, 130, 131, 132, 133, 134; 378/46, 378/90, 92, 98.4, 98.6, 98.9, 101, 103, 140, 378/901; 600/324, 381, 425, 462, 467, 479, 600/481, 483; 606/158, 194; 128/920, 922
See application file for complete search history.

(56) References Cited

U.S. PATENT DOCUMENTS 4,662,379 A * 5/1987 Macovski .................. 600/428

(Continued)

FOREIGN PATENT DOCUMENTS

DE    69117285 T2    12/1992

(Continued)

OTHER PUBLICATIONS

Hrvoje Bogunović and Sven Lončarić, "Estimating Perfusion Using X-Ray Angiography", Proceeding of the 4th International Symposium on Image and Signal Processing and Analysis, 2005, pp. 147-150.

(Continued)

*Primary Examiner*—Abolfazl Tabatabai

(57) ABSTRACT

A sequence of groups of projection images shows an object under examination comprising a vascular system and its environment. A computer determines a 2-dimensional evaluation image having a plurality of pixels based on combination images determined from the projection images of a group. The combination images have a plurality of pixels with pixel values. The sequence of the combination images shows the time characteristic of the distribution of a contrast medium in the object. The pixels of the evaluation image correspond to those of the projection images. The computer assigns each pixel, at least in a part area of the evaluation image, a type that is characteristic of whether the respective pixel corresponds to a vessel of the vascular system, a perfusion area or a background. It performs the assignment of the type on the basis of the time characteristic of the pixel values of the combination images.

19 Claims, 16 Drawing Sheets

U.S. PATENT DOCUMENTS

| | | | |
|---|---|---|---|
| 5,357,550 A | * | 10/1994 | Asahina et al. .............. 378/98.5 |
| 5,852,646 A | * | 12/1998 | Klotz et al. ..................... 378/8 |
| 2002/0072667 A1 | | 6/2002 | Kucharczyk et al. |
| 2007/0031018 A1 | | 2/2007 | Camus et al. |
| 2007/0041625 A1 | | 2/2007 | Camus et al. |

FOREIGN PATENT DOCUMENTS

| | | |
|---|---|---|
| DE | 10 2005 039 189 A1 | 2/2007 |
| DE | 102005036564 A1 | 2/2007 |
| WO | 2005092187 A1 | 10/2005 |

OTHER PUBLICATIONS

Urban Malsch, Harmut Dickhaus and Helmut Kücherer, "Quantitative Analyse von Koronarangiographischen Bildfolgen zur Bestimmung der Myokardperfusion", Bildverarbeitung für die Medizin 2003, Algorithmen-Systeme-Anwendungen, Proceedings des Workshops, Erlangen, Mar. 9-11, 2003, pp. 81-85, Springer-Verlag.

Molloi et al., "Quantification of Volumetric Coronary Blood Flow With Dual-Energy Digital Subtraction Angiography", Circulation. 1996;93:1919-1927, pp. 1-19, retrieved from Internet on May 26, 2006, http://circ.ahajournals.org/cgi/content/full/93/10/1919.

* cited by examiner

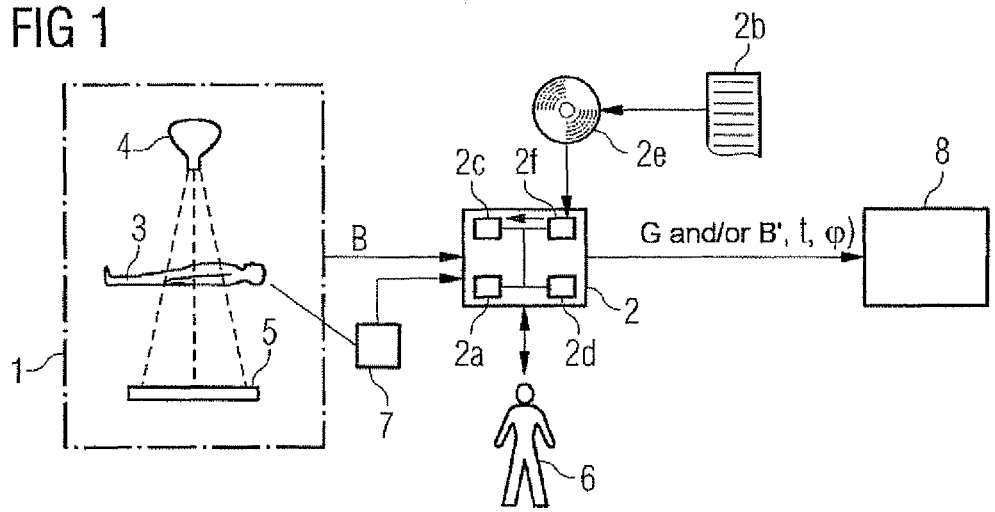
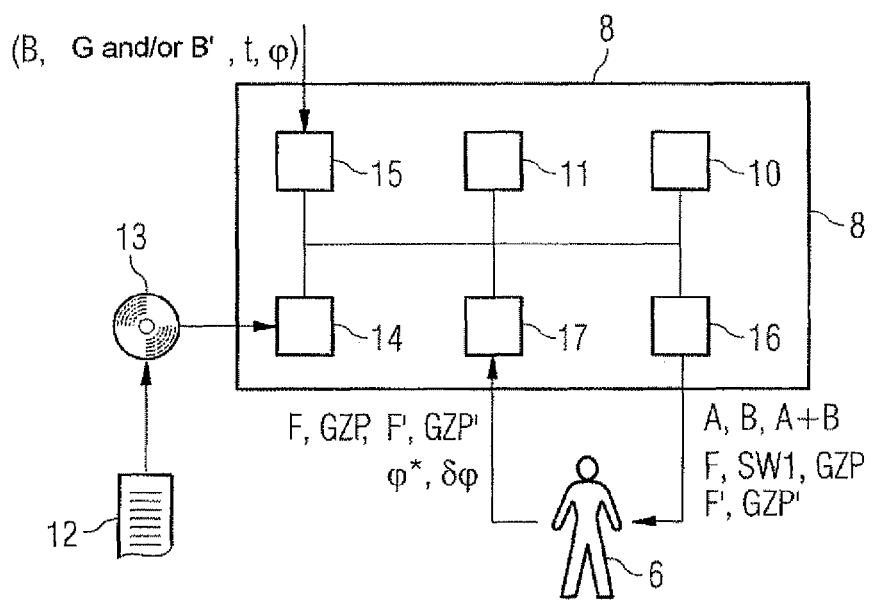

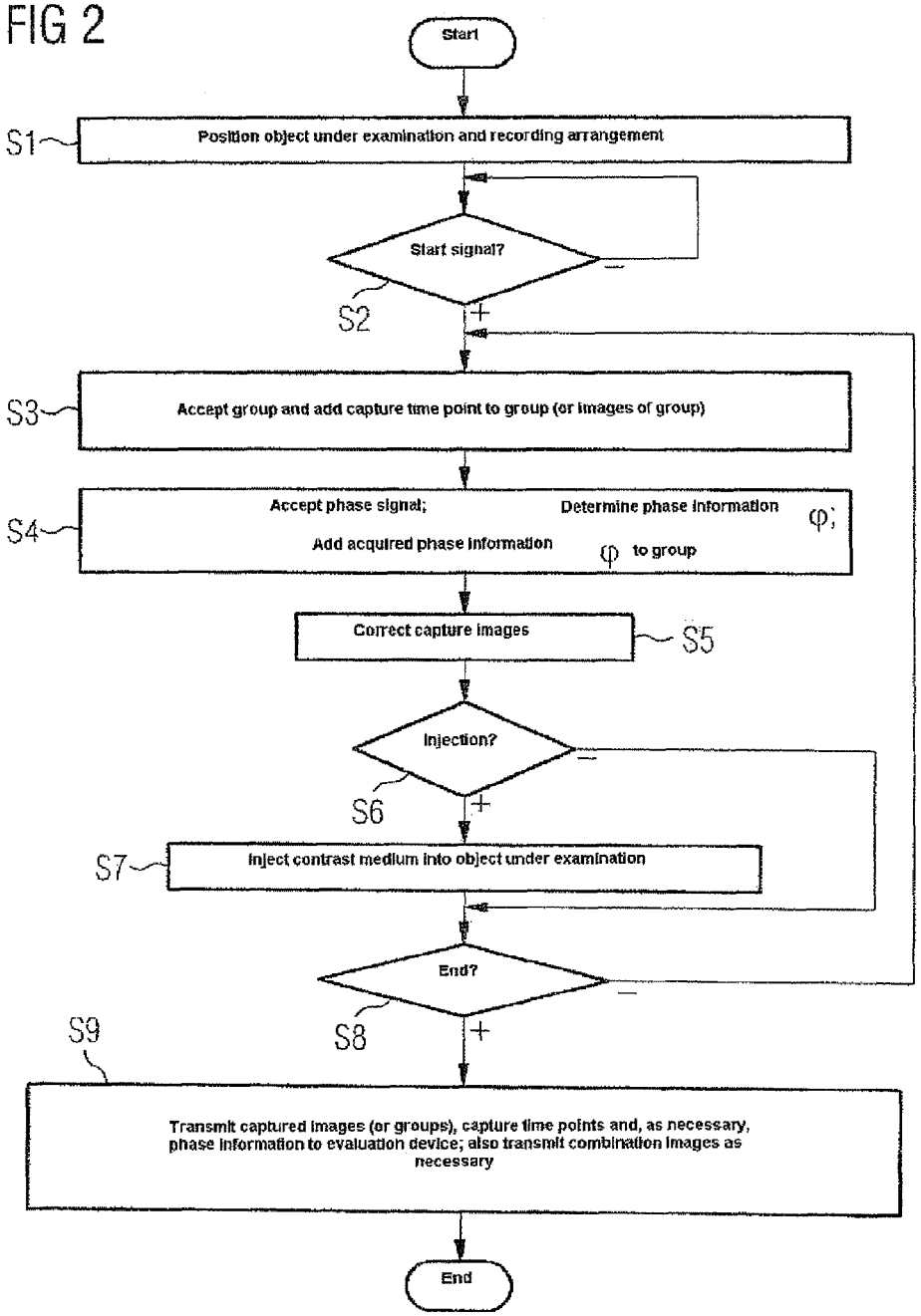

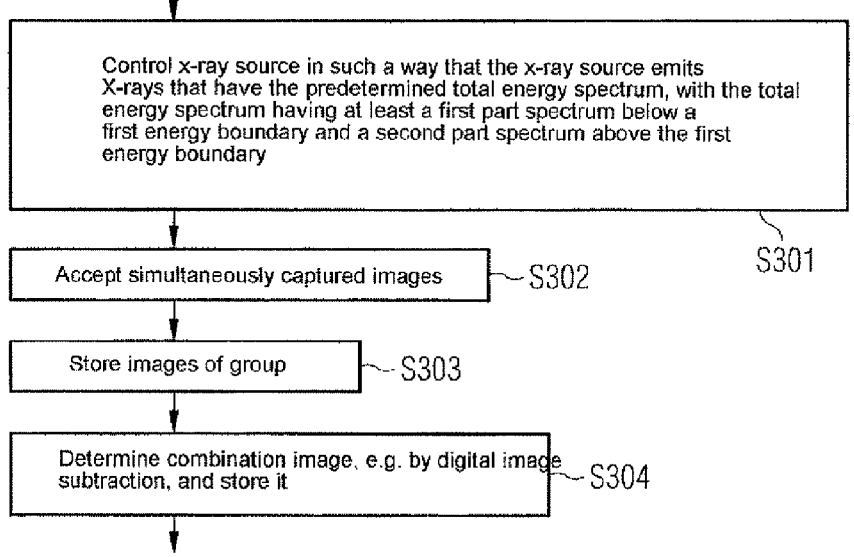
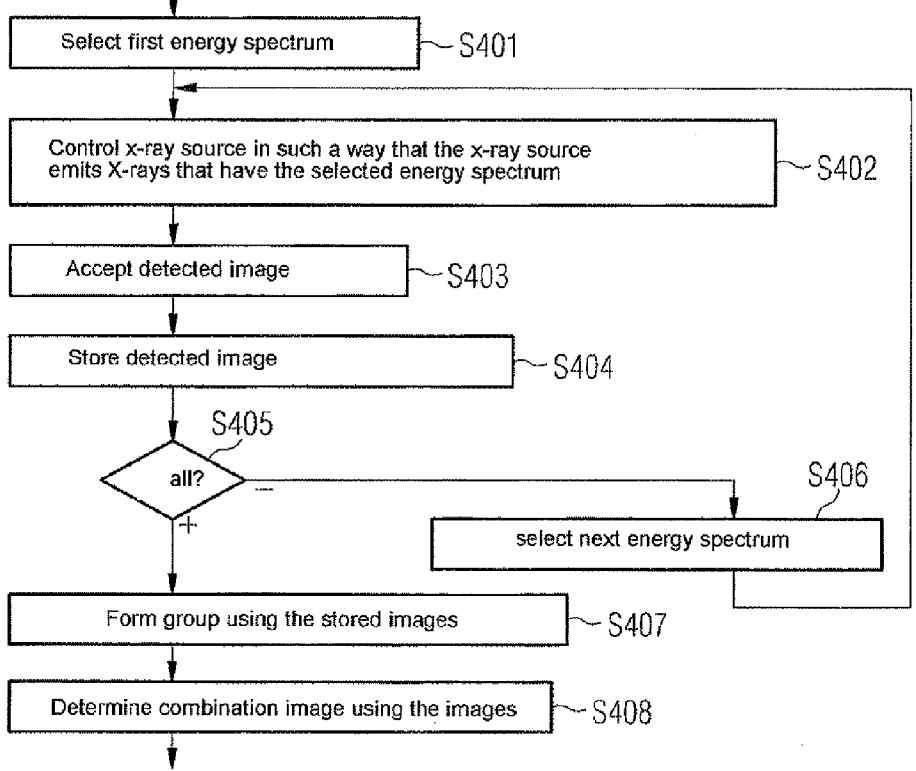

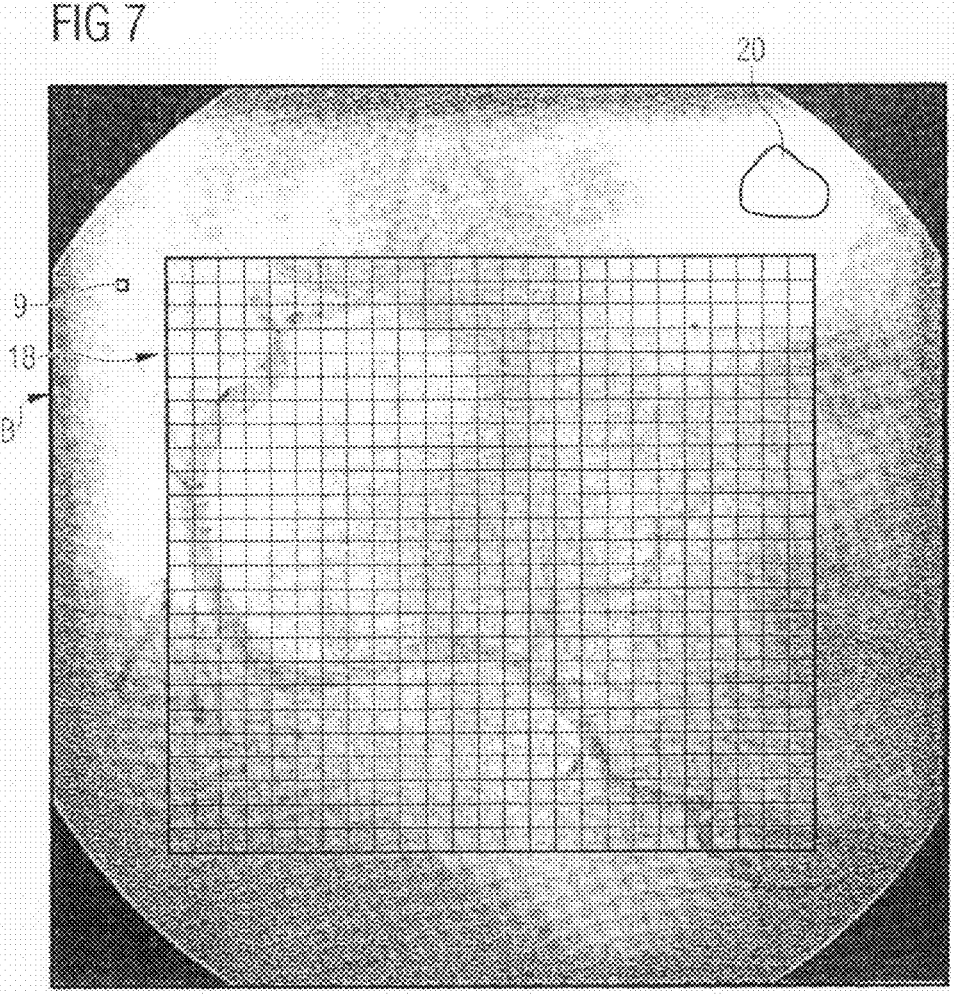

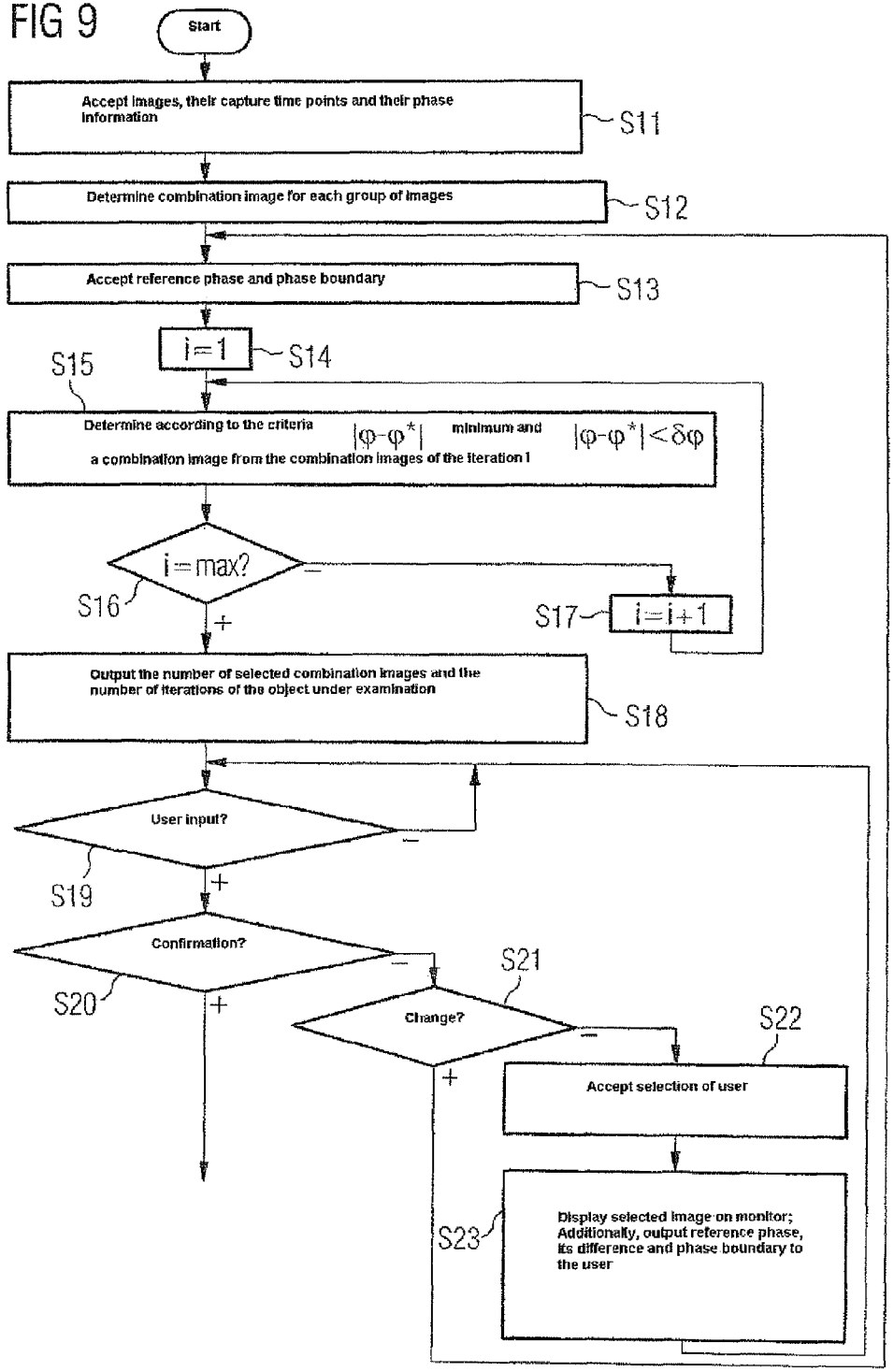

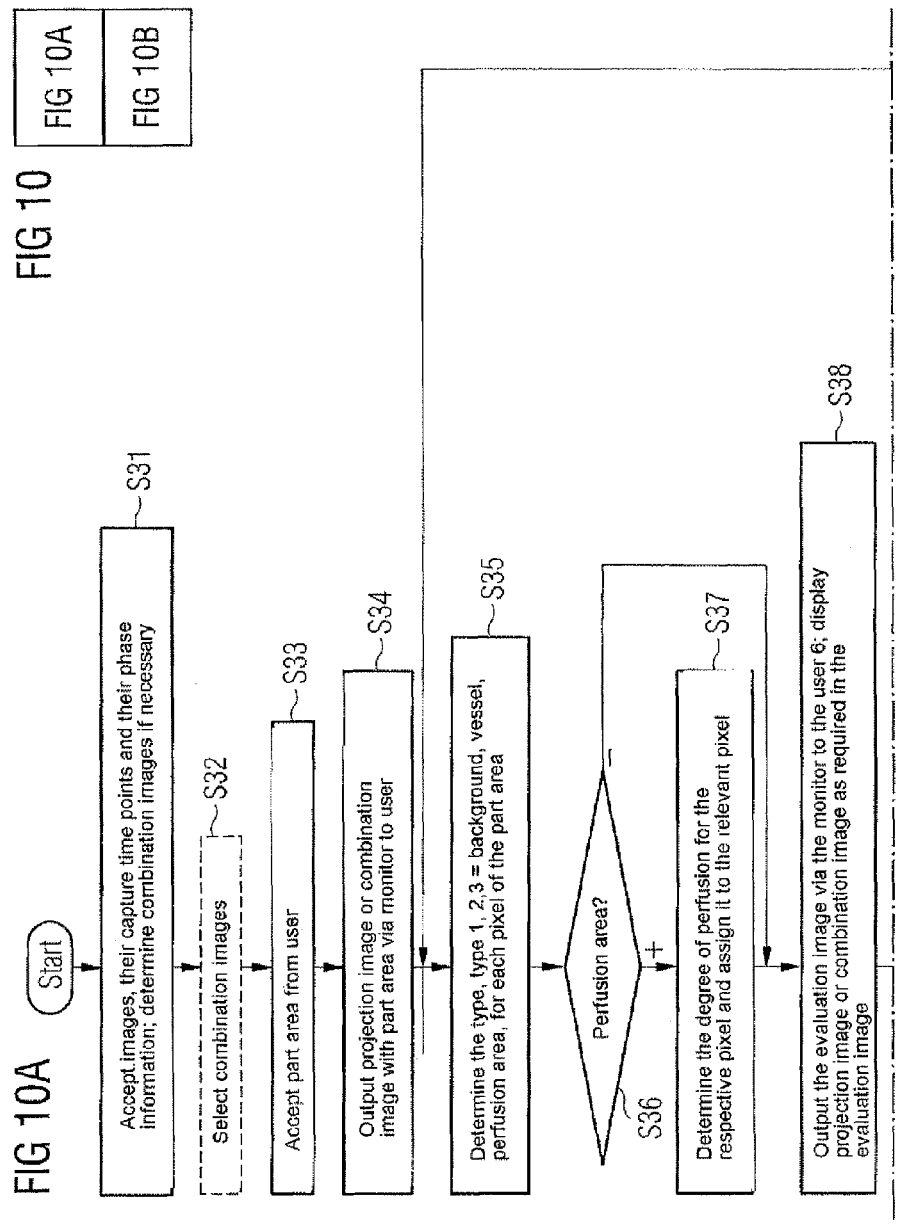

FIG 11
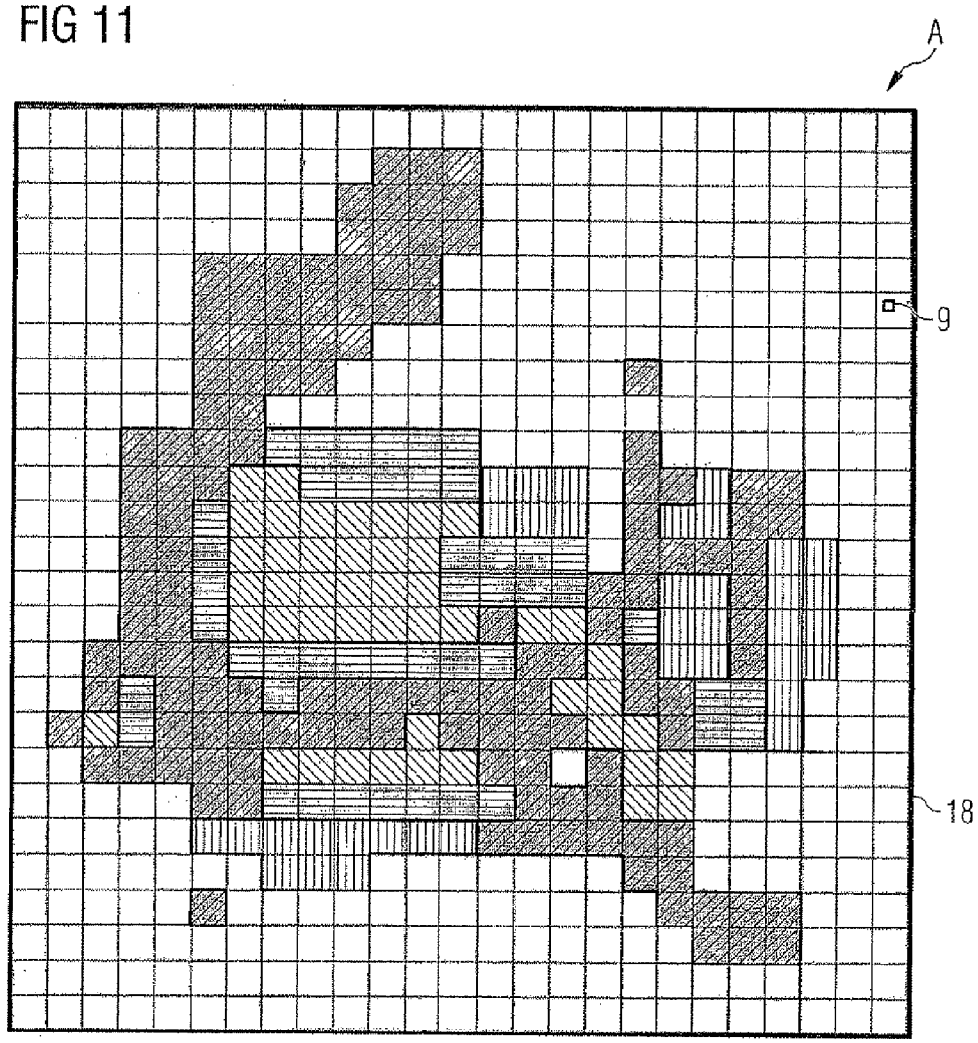
 Object vessel (e.g. dark)
Object background (e.g. light)
Perfusion low (e.g. yellow)
Perfusion medium (e.g. orange)
Perfusion high (e.g. red)
SW1=...
GZP=...
F=...
GZP'=...
F'=...

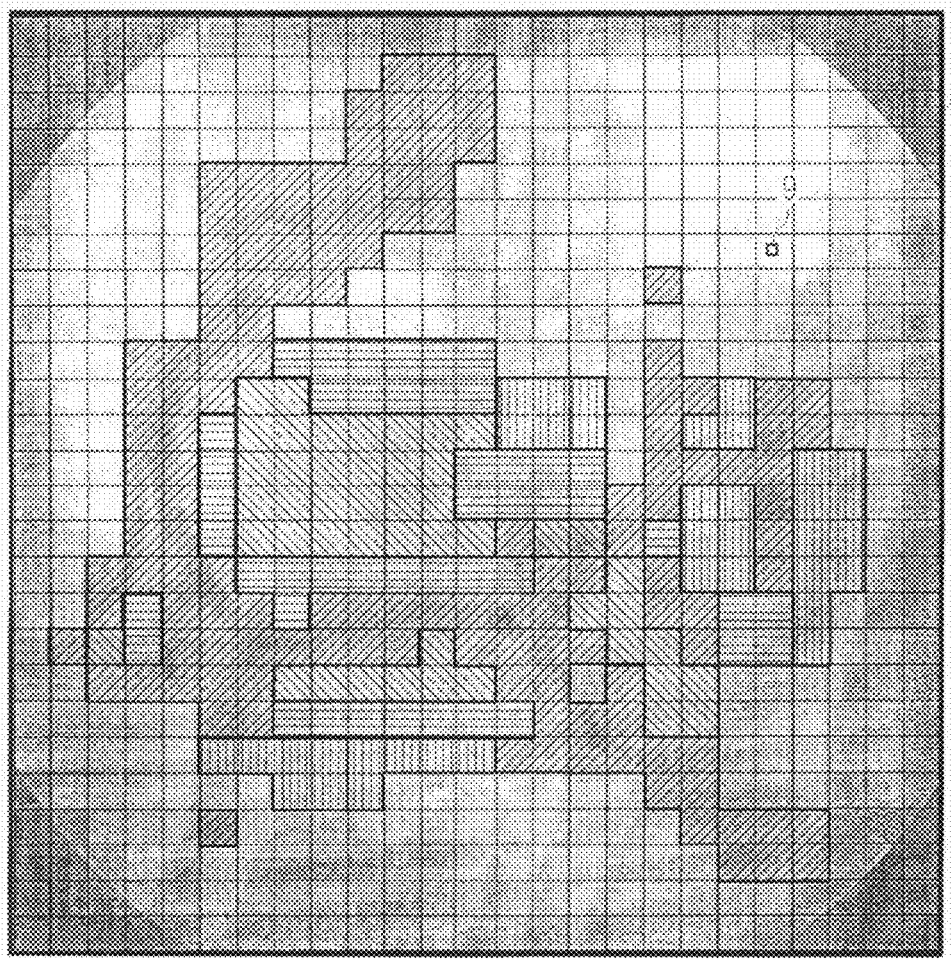
FIG 12
Object vessel
Object background
Perfusion low
Perfusion medium
Perfusion high

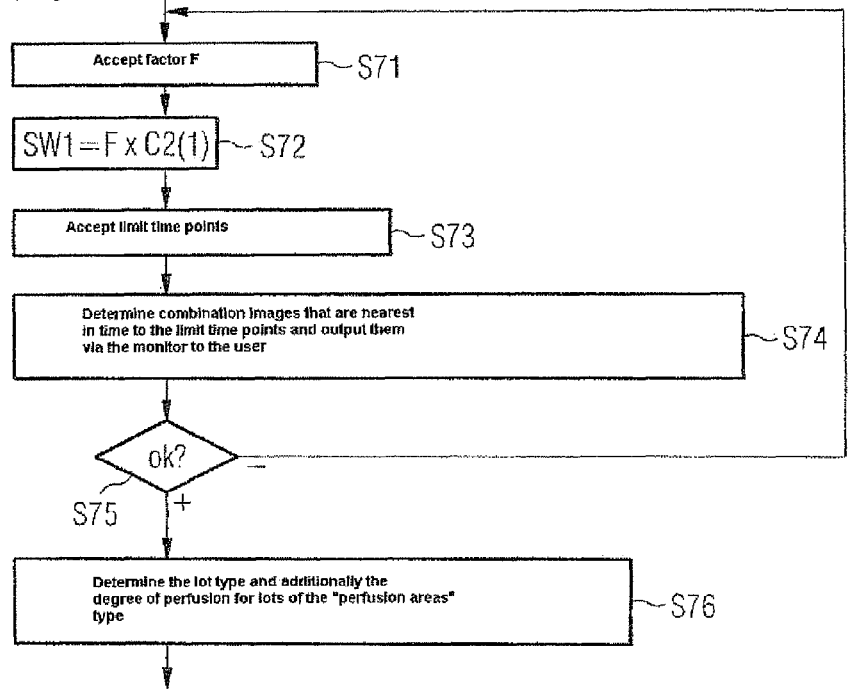
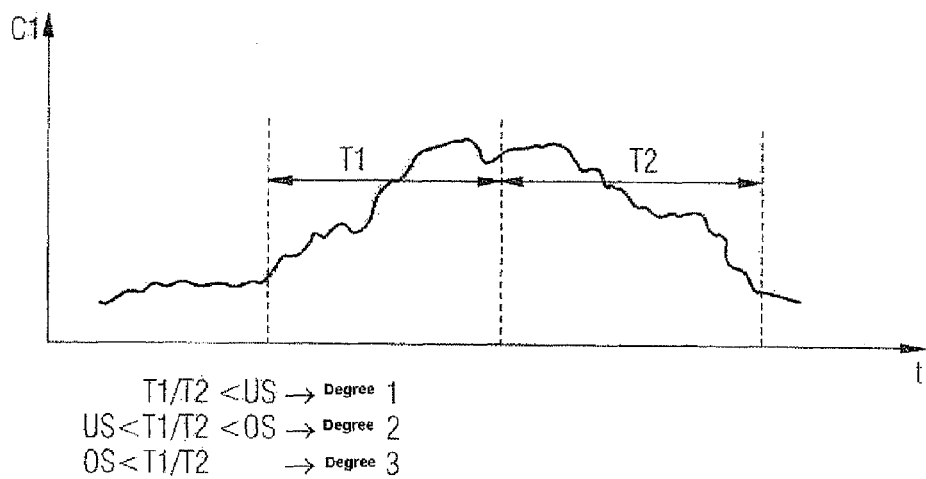

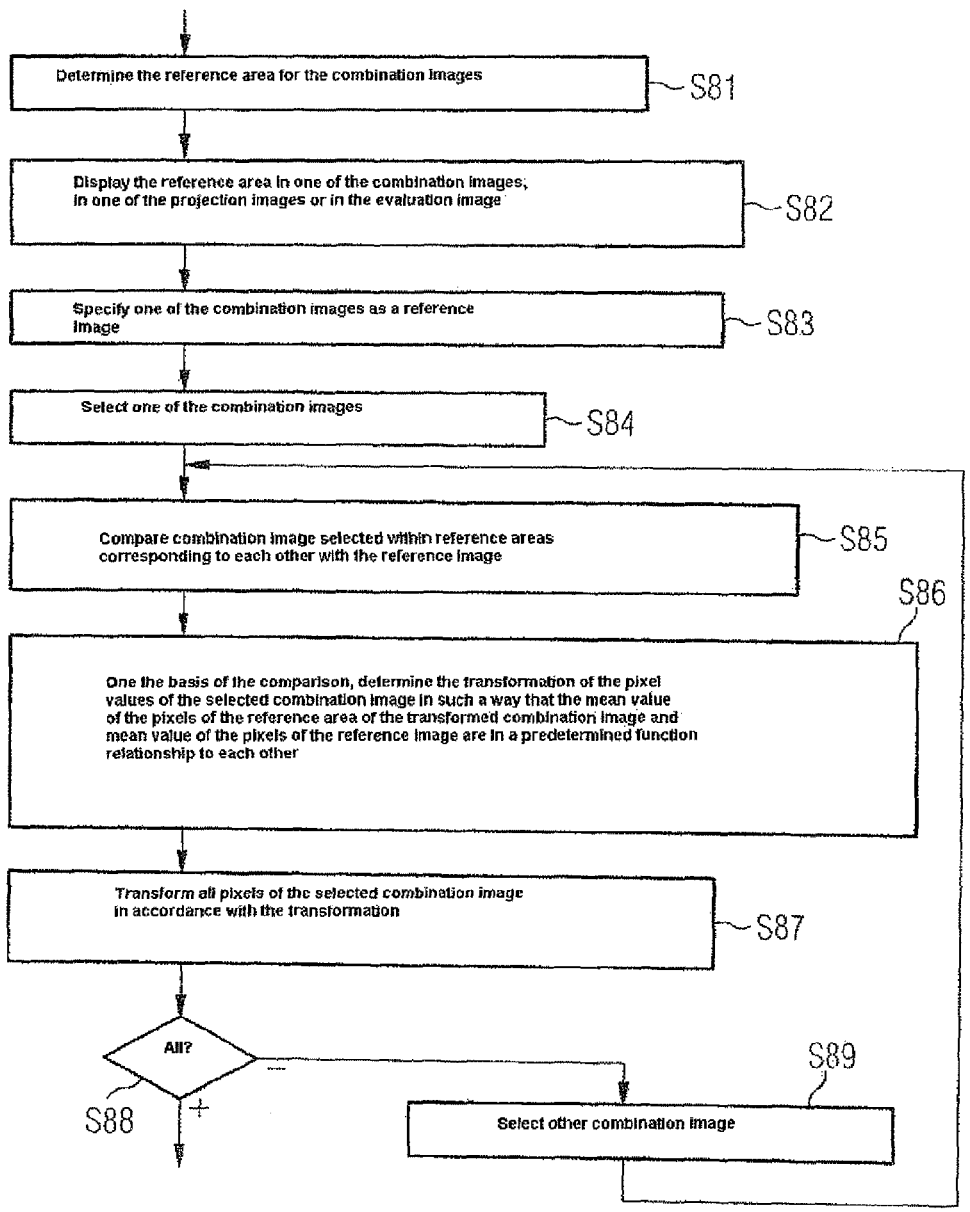

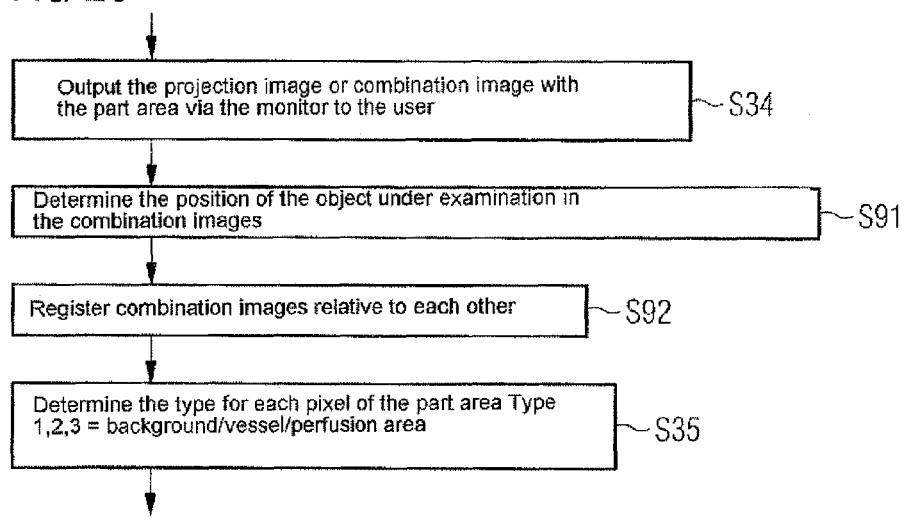

X-RAY DEVICE HAVING A DUAL ENERGY MODE AND METHOD TO ANALYZE PROJECTION IMAGES DETECTED IN THE DUAL ENERGY MODE

CROSS REFERENCE TO RELATED APPLICATIONS

The present application claims priority of German application No. 10 2006 025 423.6 filed on May 31, 2006, which is incorporated by reference herein in its entirety.

FIELD OF THE INVENTION

The present invention relates to an evaluation method for a sequence of groups of 2-dimensional projection images that show an object under examination that contains a vascular system and its environment, with each projection image having a plurality of pixels with pixel values, with the pixel values of corresponding pixels of the projection images being determined by areas of the object under examination that are at least essentially in the same location.

BACKGROUND OF THE INVENTION

Evaluation methods for projection images captured by means of x-ray systems are generally known.

An evaluation method for projection images is known from the technical article "Quantitative Analyse von Koronarangio-graphisichen Bildfolgen zur Bestimmung der Myokardperfusion"[Quantitative analysis of coronary angiographic image sequences for determining the myocardial perfusion] by Urban Malsch et al., published in "Bildverarbeitung für die Medizin 2003", Bildverarbeitung für die Medizin 2003—Algorithmen—Systeme—Anwendungen,[Image processing for medical science 2003—algorithms, systems, applications], Springer-Verlag, pages 81-85. With this evaluation method, a computer uses the projection images to determine a 2-dimensional evaluation image that has a plurality of pixels and outputs the evaluation image to a user by mean of a monitor. The pixels of the evaluation image correspond to those of the projection images. The computer uses the time characteristic of the pixel values of the projection images to assign a pixel value to the pixels of the evaluation image. The pixel value of the evaluation image is characteristic of the time point of the maximum contrast change.

A similar disclosure is given in the technical article "Estimating Perfusion Using x-ray Angiography" by Hrvoje Bogunovic and Sven Loncaric. This technical article is published in the Proceedings of the 4$^{th}$ International Symposium on Image and Signal Processing and Analysis (2005), pages 147 to 150. According to this technical article, a subtraction of a reference image from the projection images takes place.

The doctrines of the two latter-named technical articles are described in the context of angiographic examinations of coronary vessels of the human heart. This type of examination is at present one of the most important diagnostic aids of cardiology. Additional information such as the determination of the rate of flow or the myocardial perfusion is further information that can be obtained by means of angiography. The essential diagnostic evidence is the perfusion of the myocardium.

The quantification of the blood flow through the myocardium using an angiographic procedure is problematic because the coronary vessels when angiographically observed have a diameter of barely 1 mm or more. These observed vessels end in millions of tiny capillary vessels which have diameters of only a few micrometers. The flow dynamics and distribution in the capillary vessels finally determines the blood supply of the myocardium. Inference of the macroscopic blood flow of the observed coronary vessels on the dynamics and distribution of the blood flow in the capillary vessels is strictly speaking not permissible but such conclusions are, however, often drawn on this basis.

Angiographic-based heart perfusion imaging carries out long recordings, with the recordings lasting until the contrast medium has passed through the coronary vessels and is visible in the myocardium itself. This latter phase is known as "myocardial blush". The "myocardial blush" is assessed to obtain evidence of the supply of the heart with blood and, for example, to gauge the success of therapies and/or estimate the risk profile for the patient.

To make the blood flow dynamics in large vessels and in the capillary vessels measurable and therefore comparable, various gradation systems are known that divide the continuum of the possible conditions into discrete classes. Many of these classifications describe the macroscopic blood circulation and others the capillary blood circulation. The most common classifications were determined by the scientific organization "Thrombolysis in Myocardial Infarction" (TIMI). These classifications are regarded as standard. The TIMI classifications are frequently used in multicentric studies where it is particularly a question of reproducible and comparable results. These classifications are, however, complex and can be used only by expending considerable time. They are not usually used in routine clinical work.

By far the most frequently used method according to prior art is the visual estimation of the myocardial blush on the monitor. This procedure is often used for multicentric studies. A precondition for this procedure is that the angiographic recording is sufficiently long to enable the introduction and washout of the contrast medium to be detected. The visual estimation requires much experience and in practice is carried out only by TIMI-blush experts.

Procedures are also known by means of which a computer-aided attempt is made at a visual subjective-personal estimation. An example of such a method is given in the aforementioned technical articles by Urban Maltsch and Bogunovic.

Although the procedures in the aforementioned technical articles represent a good starting point they still have shortcomings. In particular, it is necessary with the procedures according to the technical articles to identify the vessels of the vascular system in the projection images in order to be able to hide these vessels when evaluating the myocardial blush. It is also necessary with the procedures according to the technical articles to operate with DSA images. This presents a distinct danger of artifacts. Computer intensive processors for movement compensation are necessary to avoid artifacts.

Evaluation methods for 2-dimensional projection images are also described in German patent application DE 10 2005 039 189.3. This patent application was still not available to the public on the date of filing of this present invention and does not represent a general prior art. This patent application has to be examined with regard to novelty only in the German patent granting procedure. The method described in patent application DE 10 2005 039 189.3 is already very effective. In particular, an automatic identification of the vessels of the vascular system is possible by means of this method. Furthermore with the evaluation method described therein it is not absolutely necessary to work with DSA images.

SUMMARY OF THE INVENTION

The object of the present invention is to provide an evaluation method and the devices corresponding herewith by means of which a simple identification of the vascular system is possible inter alia using the projection images.

The object is herewith achieved with an evaluation method in that a computer determines a 2-dimensional evaluation image, with the aid of combination images, said evaluation image has a plurality of pixels and outputs the image to a user via a monitor, that each combination image is determined with the aid of projection images of a group in each case, that each combination image has a plurality of pixels with pixel values and the sequence of combination images shows the time characteristic of the distribution of a contrast medium in the object under examination, that the pixels of the evaluation image correspond with those of the projection images, that a computer, at least in a part area of the evaluation image, assigns a type to each pixel that is characteristic of whether the particular pixel corresponds to a vessel of the vascular system, a perfused part of the environment of a vessel of the vascular system (perfusion area) or a non-perfused part of the environment of a vessel of the vascular system (background), and that the computer assigns the type on the basis of the time characteristic of the pixel values of the combination images.

The combination images are evaluated in accordance with the invention. Also an assignment to one of the "vessels", "perfusion area" and "background" types takes place by means of the evaluation of the time characteristic of the pixel values of the combination images. In contrast to the known prior art, it is no longer necessary with the present invention for the user to specify which area of the combination images corresponds to the myocardium. The computer can instead automatically carry out the type assignment on the basis of the combination images.

The evaluation method according to the invention can be universally applied. It can also be applied especially if the object under examination does not move. An example of such an object under investigation is the human brain, in which circulatory problems, as with the human heart, can occur. An acute circulatory problem of the brain is known as a "stroke".

In most cases the object under examination is an iteratively moving object under examination, e.g. the human heart. In this case, it is possible for a series of images to be initially captured and then sent to the computer. In this case, phase information relating to the object under examination can be assigned to each image of the series. The combination images in this case are selected from this series, with it being noted that the phase information assigned to the combination images can deviate by a maximum of one phase boundary from a reference phase. Both the reference phase and the phase boundary can be specified to the computer by the user.

The computer preferably determines the number of selected combination images and passes this information to the user via the monitor. This process affords the possibility of a visual check by the user to determine whether the reference phase and/or the phase boundary is/are well determined. If necessary, the total number of captured iterations of the object under examination can additionally be output.

It is possible for the user to select one of the projection images or one of the combination images and for the computer to then send the selected image together with the phase information assigned to this image and/or together with the deviation of the phase information assigned to this image to the user via the monitor. This procedure enables the user to see the magnitude of the deviation of the phase information of the output image from the reference phase.

The part area is preferably marked as such in one of the projection images, in one of the combination images or in the evaluation image. The marking can, for example, be carried out by means of a highlighted border, e.g. a black border. This makes it easy for the user to see which area is specified as the part area.

The part area can be predefined. Preferably, this is specified in advance to the computer by the user.

The computer preferably performs the type assignment using the time characteristic of the pixel values of those pixels of the combination images that lie within a 2-dimensional type evaluation core of the combination images determined by the respective pixel of the evaluation image. This minimizes any noise influence.

The type assignment is particularly simple if the computer divides at least the part area of the evaluation image into type lots each consisting of several pixels and then performs the type assignment by lots. This reduces the computing effort for the type assignment by a factor of N/M, where N is the number of pixels and M is the number of type lots. Small rectangles (especially squares), small regular triangles or small regular hexagons are normally used as type lots. Other structures are also possible. The structures can even be irregular.

The computer preferably determines the weighted or unweighted mean value and/or the maximum of the pixel values occurring in the type evaluation core for each combination image and performs the type assignment using the time characteristic of the mean value and/or of the maximum. In this way, the evaluation method can on one hand be realized relatively simply and on the other hand it is very reliable and robust. A type evaluation core can correspond especially to the respective type lot.

Preferably, the computer also determines an extent of a perfusion (degree of perfusion) for those of the pixels of the evaluation image to which it has assigned the "perfusion area" type and assigns this extent to the respective pixel.

For example, it is possible for the computer to perform the assignment of the degree of perfusion using the time characteristic of the pixel values of those pixels of the combination images that lie in a 2-dimensional extent evaluation core of the combination images determined by the respective pixel of the evaluation image.

The computer preferably divides at least the part area of the evaluation image into extent lots, each consisting of several pixels, and performs the assignment of the degree of perfusion by lots. By this means, the computing cost can be substantially reduced, similar to the type assignment.

The evaluation method according to the invention can be particularly simply implemented if the computer determines the weighted or unweighted mean value of the extent evaluation core for each combination image and assigns the degree of perfusion using the time characteristic of the mean value.

The extent evaluation core preferably corresponds to the respective extent lot.

The extent evaluation core can be identical to the type evaluation core. This simplifies the inventive evaluation method.

Preferably, the computer converts at least the degree of perfusion of the pixels of the evaluation image into color values using an assignment rule and provides the evaluation image in the form of a corresponding color-coded display to the user by means of the monitor. This makes the degree of perfusion particularly easy for the user to intuitively understand.

Both "background" and "vessel" types can also be color coded if required. These two types are however preferably shown as grey values.

If the computer outputs the assignment rule together with the (complete or partial) color-coded display to the user via the monitor, it is intellectually particularly easy for the user to assign the degree of perfusion. The assignment rule can, for example, be displayed in the evaluation image or next to the evaluation image, in its own window for instance.

The evaluation method according to the invention can still be further optimized. For example, one of the combination images can be allocated as a reference image and the computer can compare a reference area of the combination images with a corresponding reference area of the reference image. In this case, the computer can use the comparison to determine a transformation of pixel values that is valid for all pixels of the respective combination image, so that the mean value of the pixel values of the reference area of the transformed combination image and a mean value of the pixel values of the reference area of the reference image are in a predetermined functional relationship. In this case, the computer transforms the pixel values of the respective combination image corresponding to this transformation. By this means, differences in intensity in the combination images that result because of the non-reproducible operating parameters during the capture of the projection images can be at least partially compensated for.

Preferably, the computer displays the reference area in one of the projection images in one of the combination images or in the evaluation image. In this way the user can intuitively determine the image area that was used for the transformation. Based on his intellectual understanding of the displayed image, the user can assess whether the reference area is properly determined.

It is possible for the computer to automatically determine the reference area. For example it is possible for the computer to determine the reference area using the pixels of the evaluation image to which it has assigned the "background" type. When determining the reference area, the computer can alternatively or additionally take account of information regarding the recording geometry on which the projection images are based and the injection point of the contrast medium into the object under examination.

As an alternative to the determination of the reference area by the computer, it is possible for the reference area to be specified to the computer by the user.

Preferably, the computer provides at least the determination criteria on the basis of which it has determined the type assignment of at least the part area of the evaluation image, together with the evaluation image, to the user by mean of the monitor. This makes checking by the user easy.

Preferably, the determination criteria can be interactively changed by the user. In this case, the computer redefines the evaluation image when the determination criteria are changed. This procedure enables the determination of the criteria to be easily optimized by the user.

Preferably, the computer displays one of the projection images or one of the combination images in the evaluation image. In this way, the user can easily detect the position of the vessel. The user can therefore check whether the computer has correctly carried out the type assignment.

The object under examination is depicted in the projection images of the groups at a position that is at least essentially the same as for the projection images of the respective group. The position can, however, vary from group to group. If the object under examination is the human heart, it is, for example, possible that the heart does not always take up the same position after each heartbeat. Furthermore, a further movement, such as a movement caused by breathing, can be superimposed on the heartbeat. For this reason, the computer preferably determines the position of the object under examination in the combination images and registers the combination images relative to each other.

To determine the position of the object under examination in the combination images, the computer can, for example, determine, for each group, the position of the object under examination in the projection images and/or in the combination image using at least one of the projection images or the combination image of the respective group. In particular, the position, for example of the diaphragm or of ribs, can be determined in one of the projection images that was taken at an energy spectrum below the first energy boundary and determine the position of the heart on the basis of this information. Alternatively or additionally, the position of the heart can be inferred in the projection image that was captured at the energy spectrum above the first energy boundary, in individual cases on the basis of vessels filled with a contrast medium, particularly at vascular branches.

As an alternative to determining the position using the projection images and/or the combination image, it is possible for additional information corresponding to the position and not contained in the projection images to be assigned to the groups. For example, information regarding the respiratory state (inhaled, exhaled, corresponding intermediate state) can have been obtained by means of a suitable sensor and sent to the control device. In this case, the control device can assign this information to the respective group. Using this information, the computer in this case can determine the position of the object under examination in the projection images and/or combination image of the respective group using the additional information.

It is possible for the combination images to be specified to the computer. Preferably, however, the computer itself determines the combination images using the projection images.

BRIEF DESCRIPTION OF THE DRAWINGS

Further advantages and details result from the following description of the exemplary embodiments, in conjunction with the drawings. The drawings are as follows.

FIG. 1 A block diagram of a recording arrangement, of a control computer and of an evaluation device
FIGS. 2-4 A flow diagram
FIGS. 5, 6 Time diagrams
FIG. 7 Example of a projection image
FIG. 8 A block diagram of an evaluation device
FIGS. 9, 10 Flow diagrams
FIG. 11 An evaluation image
FIG. 12 The evaluation image from FIG. 11 with a superimposed image
FIG. 13 A flow diagram
FIG. 14 An intermediate image derived from a combination image
FIGS. 15, 16 Time characteristics of characteristic variables
FIG. 17 A flow diagram
FIG. 18 A time characteristic of a mean value
FIGS. 19, 20 Flow diagrams

DETAILED DESCRIPTION OF THE INVENTION

Figure 5:
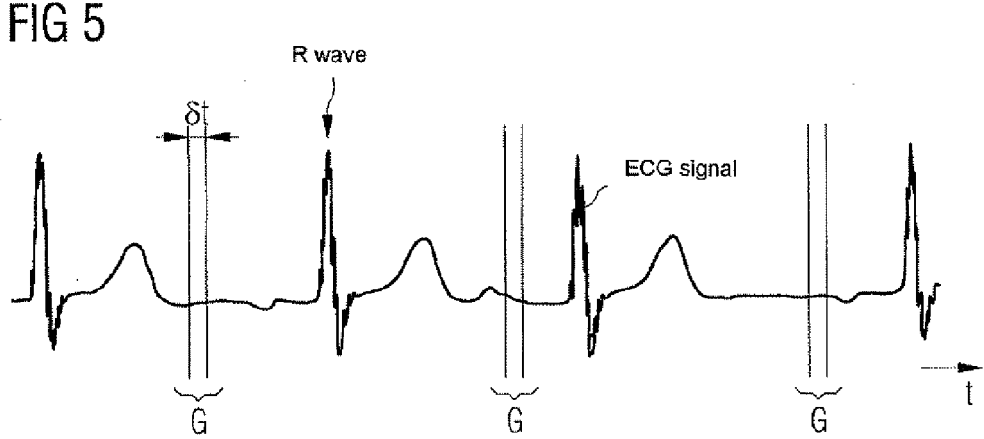

FIG. 1 is a schematic of an x-ray system. According to FIG. 1, a recording device 1 is controlled by a control device 2. Images B of an object under examination 3 are captured by means of the recording device 1. In this present case in which the object under examination 3 is a human, images B of the heart or of the brain of the human 3 are, for example, captured.

To capture the images B, the recording arrangement 1 has an x-ray source 4 and the x-ray detector 5.

The control device 2 is preferably designed as a software-programmed control device 2. It has a processor unit 2a on which in operation a control program 2b is executed. The control program 2b determines the operating mode of the control device 2 and therefore also of the overall x-ray system. The control program 2b is stored in a mass storage unit 2c of the control device 2. It can be called up through an input/output interface 2d by means of a suitable call-up command by an operator 6 of the x-ray system. If such a call-up takes place, the control program 2b is executed and the x-ray system is operated in the manner described in more detail in the following.

The control program 2b must have been stored in the control device 2. For this purpose, a data carrier 2e on which the control program 2b is stored can, for example, have a data link to the control device 2 through a corresponding interface 2f of the control device 2. In this case, the control device 2 is able to accept the control program 2b from the data carrier 2e (e.g. a CD-ROM) and store it in the mass storage unit 2c.

To capture the images B, the object under examination 3 and the recording arrangement 1 are, in step S1, first positioned according to FIG. 2. The positioning takes place in such a way that the object under examination 3 is arranged between the x-ray source 4 and the x-ray detector 5. The positioning can depend upon which region (heart, brain, etc) of the object under examination 3 is to be recorded and which part of the region to be recorded is particularly relevant. For example, the positioning can depend on which coronary artery (RCA, LAD, LCX) is to be observed. Step S1 can be performed purely manually by the operator 6. Alternatively, step S1 can be performed fully automatically by the control unit 2. Interaction between the operator 6 and the control unit 2 is also possible.

The performance of step S1 can be linked with a recording of checking images. The recording of images is not relevant in the context of this present invention and for this reason is not explained further in the following.

In step S2, the control device 2 waits for a start signal from the operator 6. On receipt of the start signal, the x-ray detector 5 captures a group G of images B of the object under examination 3 and supplies group G to the control device 2. The control device 2 accepts group G in step S3 and adds a capture time point t to group G (or the images B of group G). Step S3 is explained in more detail later in conjunction with FIGS. 3 to 6.

If the x-ray detector 5 is designed as an energy-resolving x-ray detector 5, step S3, i.e. the capture of group G of images B, can be configured as explained in the following in conjunction with FIG. 3. If the x-ray detector 5 is not designed as an energy-resolving x-ray detector 5, step S3 can be configured as explained in more detail in the following in conjunction with FIGS. 4 to 6.

According to FIG. 3, the control device 2 controls the x-ray source 4 in step S301 in such a way that the x-ray source 4 emits x-rays that have a predetermined total energy spectrum. The total energy spectrum has at least two part spectra. A first part spectra lies below a first energy boundary. The second part spectrum lies above the first energy boundary.

If necessary, the total spectrum can have more than two part spectra, for example three part spectra. In this case, at least two of the part spectra are located above or below the first energy boundary. These two latter-named energy spectra straddle a second energy boundary.

The first energy boundary is at least 40 keV. Preferably it is a maximum of 75 keV. In particular the first energy boundary can lie between 45 and 70 keV, for example between 50 and 65 keV. If possible, it should correspond exactly to the K edge of the contact medium used. In the context of this present invention, the use of one of the elements dysprosium, erbium, ytterbium and especially gadolinium is preferred as a contrast medium.

The second energy boundary can, if present, be either above or below the first energy boundary. Preferably it lies at at least 30 keV, especially at at least 35 keV. Furthermore, it preferably lies at a maximum of 75 keV, especially at a maximum of 70 keV.

With the method in FIG. 3, the x-ray detector 5 detects one image B, separately in each case, for each part spectrum. The detected images B are applied to the control device 2. Together they form a group G of images B. In step S302, the control device 2 accepts the simultaneously captured images B and, in step S303, forms the respective group G from these images B. Furthermore, in step S303 it stores the images B of group G. Alternatively or additionally, it is possible for the control unit 2, by using the images B of group G, to determine a combination image B', especially by digital image subtraction, and to store the combination image B'. This takes place as necessary in step S304.

According to FIG. 4, the control device 2 selects a first energy spectrum in step S401. In step S402, the control device 2 controls the x-ray source 4 in such a way that the x-ray source 4 emits x-rays that have the selected energy spectrum.

The x-ray detector 5 captures an image B and sends it to the control device 2. In step S403, the control device 2 accepts the image B detected by the x-ray detector 5. In step S404, it stores the accepted image B.

In step S405, the control device 2 checks whether it has already set all the energy spectra. If this is not the case, the control unit goes to step S406. In step S406, the control unit 2 selects the next energy spectrum. From step S406 the control unit 2 returns to step S402.

If an image B has already been captured for all energy spectra, the control device 2 goes to step S407. In step S407, the control unit 2 uses the images B stored in step S404 to form a group G. Alternatively or in addition, the control unit 2 can perform step S408. In step S408, the control unit 2 determines a combination image B' using the images B of the respective group G. Step S408 is optional. It corresponds with regard to contact to S304.

The energy spectra of FIG. 4 correspond to the part spectra of FIG. 3.

With the procedure according to FIG. 4, the capture of the images B of group G does not take place simultaneously but instead in succession. The individual images B of the respective group G are thus captured at intervals δt. According to FIGS. 5 and 6, the interval δt is substantially less than a typical iteration period of the object under examination 3. As a rule, the interval δt amounts to a few milliseconds, for example one to ten milliseconds. The movement, e.g. of the heart (as an example of an object under examination 3 that is moving iteratively) is practically negligible in this interval.

The case is dealt with in more detail in the following in which each group G of images B contains exactly two images B. The arrangements can simply be extended to a case where there are more than two images B per group G.

The first energy barrier is defined in such a way that it corresponds as accurately as possible to the K edge of the contrast medium that is used. One of the images B of the particular group G shows the contrast medium and the surrounding tissue; the other image B shows only the tissue. By means of a digital image subtraction of both images B of group G from each other, the contrast medium in the combination image B' can be more clearly highlighted.

Below approximately 30 to 35 keV, human tissue absorbs x-ray energy relatively strongly. For this reason, the first energy boundary is preferably at at least 40 keV. The result of this is that the image B, which contains signal components of the contrast medium, contains only relatively small proportions of the tissue. The digital image subtraction is thus particularly good. Furthermore, because of the simultaneous or quasi-simultaneous recording of the images B of the respective group G, only very few artifacts occur. The combination images B' thus clearly show the contrast medium and show the other components of the object under examination 3 or artifacts only to a very slight extent.

If the object under examination 3 or the relevant part of the object under examination 3 is to move iteratively, the control unit 2, in step S4, furthermore receives a phase signal of the object under examination 3 from a corresponding detection device 7. Also as part of step S4, the control device 2 determines corresponding phase information φ and adds the phase information φ to the captured group G. For example, the control device 2 can receive an ECG signal as part of step S4 and from this derive the phase information φ. The control device 2 can also control, as required, the recording arrangement 1 using the supplied phase signal in such a way that the capture of group G takes place only at one or more predetermined phase positions of the object under examination 3, for example only 0.3 and 0.6 seconds after the R wave of an ECG signal.

The object under examination 3 is usually not influenced in its iterative movement from outside. If, for example, the human heart 3 has a very irregular beat, an external excitation of the heart can, however, be selectively applied using a heart pacemaker in order to force a regular heartbeat.

In step S5, the control device 2 collects the captured images B. The control device 2 corrects the captured images B preferably exclusively by detector-specific corrections but does not carry out any other image processing. For example, it preferably does not apply any kind of noise reduction measures.

In step S6, a check is carried out to determine whether an injection of a contrast medium should take place. If this check is positive, the contrast medium is injected into the object under examination 3 in step S7. Steps S6 and S7 can, analogous to step S1, be performed by the user 6 himself, fully automatically by the control device 2 or else be performed by the user 6 but with support from the control device 2.

In a step S8, the control device 2 checks whether the acquisition of the images B should be ended. If this is not the case, the control device 2 returns to step S3, otherwise, in step S9, it transmits the captured images B (i.e. groups G), preferably corrected by detector-specific corrections, their capture time points t and, as necessary, also their phase information φ to an evaluation device 8. As an alternative to the transmission of the images B, of the capture time points t and of the phase information (p as part of the subsequent step S9, the transmission can also take place by groups or by images, i.e. between steps S5 and S6. Furthermore, the combination images B' can also be transmitted as required to the evaluation unit 8.

The other details of the method sketched above are shown only roughly because they are of only secondary importance within the context of this invention. Thus, for example, the manual, fully automatic or computer-aided setting of the recording parameters of the recording arrangement 1 (e.g. image rate, image pre-processing, positioning, etc.) are naturally assumed. Also, any calibration of the recording arrangement 1 that might be necessary is not further described. Furthermore, it is obvious that the capture of groups G must take place over a sufficiently long time period, i.e. beginning before the injection of the contrast medium and ending after the washing out of the contrast medium.

FIG. 7 shows an example of one of the captured images B. It can be seen from FIG. 7 that image B is 2-dimensional and contains a plurality of pixels 9. The resolution of the image B is usually even so high that in the image B shown the individual pixels 9 can no longer be detected. One of the pixels 9 is shown appropriately marked in the image B shown in FIG. 7 purely by way of example. Each pixel 9 has a pixel value of between 0 and 255 ($=2^8-1$).

From FIG. 7, it can also be seen that the object under examination 3 contains a vascular system and its environment. On the basis of the circumstance that the groups G in total form a time sequence, the combination images B' equally also show the time characteristic of the distribution of the contrast medium in the object under examination 3.

As shown in FIG. 8, the evaluation device 8, which in principle can be identical to the control device 2, mainly consists of a processing unit 10 and a mass storage unit 11. A computer program 12 is stored in the mass storage unit 11. After the computer program 12 is called up, the evaluation unit 8 performs an evaluation method which is described in detail in the following. The evaluation device 8 represents a computer within the meaning of this invention.

It should be mentioned in advance that the computer program 12 must have been provided to the evaluation unit 8 beforehand. The provision can, for example, take place by means of a suitable data carrier 13 (e.g. a CD-ROM) on which the computer program 12 is stored. The data carrier 13 is coupled to the evaluation device 8 by means of a suitable interface 14. This enables the computer program 12 stored on the data carrier 13 to be read and stored in the mass storage unit 11 of the evaluation unit 8.

A case where the groups G of images B are supplied to the evaluation unit 8 is described in the following. In this context, it is assumed that the capture time point t of the images B is constant per group G. This assumption is permissible because any interval present δt is substantially smaller than the iteration periods of the object under examination 3.

According to FIG. 9, the evaluation unit 8, in step S11, accepts the images, their capture time points t and phase information φ via a suitable interface 15.

It is possible that the accepted images captured by the x-ray detector 5 are only processed images B. In this case, the evaluation unit 8 in step S12 determines the corresponding combination image B' for each group G of images B. The determination of the respective combination image B' takes place as already described above in conjunction with steps S304 and S408.

As an alternative, it is possible that the received images are already the combination images B'. In this case, step S12 can be omitted.

If the object under examination 3 was not moved during the capture of images B (for example because images B were taken from the brain of the human 3) or due to suitable triggering of the recording (for example always 0.6 seconds after the R wave of the ECG), the images B always show the object under examination 3 in the same phase position, all the combination images B' can subsequently be used for the evaluation described later. Otherwise a suitable selection must be made. This selection is explained in more detail in the following in conjunction with FIGS. 8 and 9.

To select the combination images B', the selection criteria φ* and δφ corresponding to the evaluation device 8 must be known, i.e. a reference phase angle φ* and a phase boundary δφ. In this case, it is possible that the reference phase φ* and the phase boundary δφ are stored within the evaluation device 8. Preferably, the reference phase φ* and the phase boundary δφ of the evaluation device 8 are specified according to FIG. 9 in step S13 by the user 6 by means of a suitable input device 17.

For example, it is possible for the user 6 to scroll through corresponding inputs in the captured sequence of groups G or in the corresponding combination images B' and to select one of the groups (i. The phase information φ of group G selected in this way, for example, determines the reference phase φ*, the distance to the directly succeeding group G and the phase boundary δφ for the immediately preceding group G. It is also possible as an alternative for the user 6 to explicitly specify the relevant values φ*, δφ. Finally, it is possible for the evaluation device 8 to output the ECG signal via a monitor 16 to the user 6 and for the user 6 to set suitable markings in the ECG signal. In all cases, the user 6 can predefine the φ* and δφ values alternatively as absolute time values or as relative phase values.

The actual selection of the combination images B' from the complete series of combination images B' takes place in steps S14 to S17. For this purpose, an index i is first set to the value one in step S14.

Within the combination images B' of the iteration i of the object under examination 3, the evaluation device 8 normally, in step S15, determines one (exceptionally also none) to be a selected combination image B'. In particular, it searches, in step S15, for the image of the combination images B' for which the amount of the difference of the phase information φ is the minimum relative to the reference phase φ*. If this difference is less than the phase boundary δφ, the corresponding combination image B' is selected. Otherwise it is not selected. If necessary, the evaluation device 8 notes when it could not select a combination image B' for a specific value of the index i.

In step S16, the evaluation device 8 checks whether the index i has already reached its maximum value. If this is not the case, the evaluation device 8 increments the index i in step S17 and returns to step S15. Otherwise, the selection of the combination images B' is ended.

As part of the following explanations, it is assumed that the images B on the basis of which the combination images B' were determined were all captured, for example, in one respiration holding phase. In this case, it is guaranteed by the procedure described above that the pixel values of corresponding pixels 9 of the combination images B' are determined in areas of the object under investigation 3 that are at least essentially in the same location. This applies even though the object under examination 3 may have iteratively moved (for example there has been a heartbeat).

In step S18 the evaluation device 8 outputs the number of selected combination images B' and the number of iterations of the object under examination 3 via the monitor 16 to the user 6. The user 6 can thus see whether he has made a good choice for the reference phase φ* and/or the phase boundary δφ.

In step S19, the evaluation device 8 waits for a user input. If such an input takes place, the evaluation device 8 checks, in step S20, whether this input is a confirmation by the user 6. If this is the case, the selection of combination images B' is completed. The actual evaluation method can continue.

If the input of the user 6 was not a confirmation, the evaluation device 8 checks, in step S21, whether the user 6 has entered a wish to change the reference phase φ* and/or the phase boundary δφ. If this is the case, the evaluation device 8 returns to step S13.

Otherwise the user 6 has input a wish for the display of an image. In this case, the evaluation device 8 in step S22, accepts a corresponding selection from the user 6. In step S23, it displays the selected image on the monitor 16. Together with the selected image, it also outputs the corresponding phase information φ of the selected image, the reference phase φ*, their difference and the phase boundary δφ via the monitor 16 to the user 6. The selected image can alternatively be a projection image B or one of the combination images B'.

It would also be possible, if required, to display the complete representation of the phase response and the phase information φ of all combination images B' at the same time.

For the sake of completeness it should be mentioned that steps S13 to S23 are only useful and/or necessary if a choice of combination images B' has to be made from the complete series of combination images B'. If on the other hand, all determined combination images B' are a priori already suitable, steps S13 to S23 can be omitted.

Furthermore, it should also be mentioned that as an alternative to the above procedure described in conjunction with FIG. 9, it is also possible to specify in advance suitable intervals for the phase information φ and to determine the number of possible combination images B' for each interval. In this case, the evaluation device 8 can output a list or table by means of which the user 6 can see how many combination images B' are available to him for each phase interval in each case. In this case, all that is required is that the user 6 selects from the phase intervals he requires.

Figure 10B:
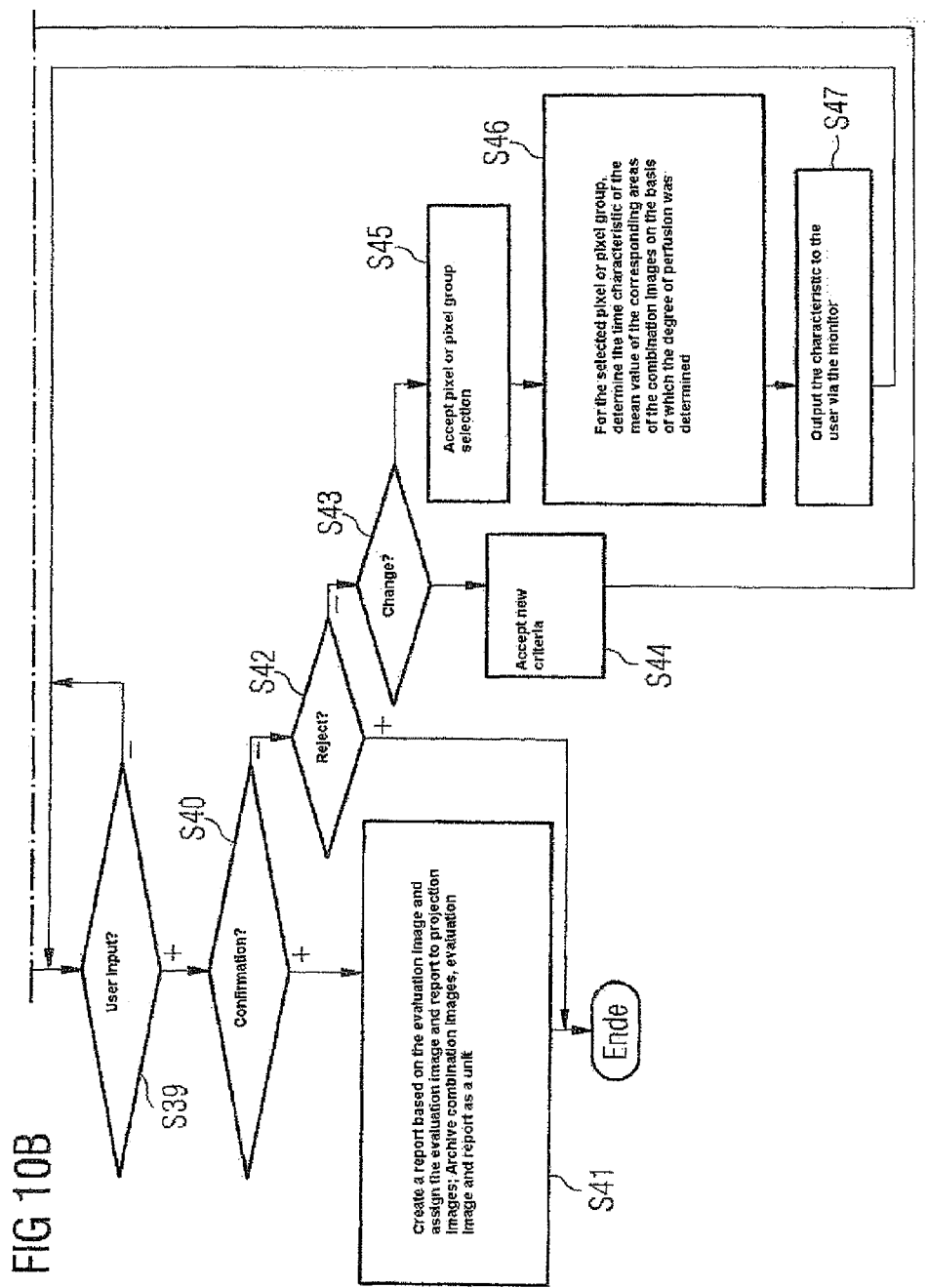

When the selection of combination images B' from the complete series of combination images B' has been completed, the procedure continues as in FIG. 10. Steps S31 and S32 of FIG. 10, in this case correspond to steps S11 and S12 on one hand and steps S13 to S23 of FIG. 9 on the other hand. Because it is only optional, step S32 is shown only by a broken line in FIG. 10.

In the context of the following illustration, only suitable combination images B' are ever considered. If a selection is made from the totality of all combination images B' according to steps S14 to S17 then the following explanation refers only to only those combination images B' which were selected in steps S14 to S17.

In step S33, the evaluation device 8 receives a part area 18 from the user 6. The evaluation device 8, in step S34, displays the part area 18 in one of the projection images B or in one of the combination images B' and outputs this image B or B', together with the marking of the part area 18, via the monitor 16 to the user 6. The part area 18 is, for example, also shown in FIG. 7. It corresponds to the black frame 18 shown there.

In step S35, the computer 8 determines the type for each pixel 9 that lies within the specified part area 18. Type 1 corresponds to a background. Type 2 corresponds to a vessel and type 3 to a perfusion area.

In step S36, the evaluation device 8 checks, for each pixel 9 of the part area 18, whether the "perfusion area" type was assigned to this pixel 9. If this is the case, the evaluation device 8, in step S37, determines a degree of perfusion (i.e. an extent of the perfusion) for the respective pixel 9 and assigns it to the relevant pixel 9.

The assignment of the particular type and, as necessary, also of the degree of perfusion to the individual pixels defines an evaluation image A. Based on the type of creation of the evaluation image A, each pixel 9 of the evaluation image A corresponds to the relevant pixels 9 of the combination images B' and also to the projection images B. In particular, the evaluation image A is also 2-dimensional and has a plurality of pixels 9. The evaluation image A is output by the evaluation device 8 during a step S38 via the monitor 16 to the user 6.

Steps S35 to S37 refer to the actual core of this present invention. Further details of this are given later.

FIG. 11 shows an example of an evaluation image A. According to FIG. 11, the evaluation device 8 has converted the degree of perfusion into color values on the basis of an assignment rule. The evaluation device 8 thus outputs the perfusion area of the evaluation image A in the form of a color-coded display via the monitor 16 to the user 6. The assignment rule, as shown in FIG. 11, can be output by the evaluation device 8, together with the color-coded display as necessary, via the monitor 16 to the user 6.

It is possible that the evaluation device 8 color codes not only the degree of perfusion but also both types "background" and "vessel". Preferably, these two types are displayed as grey values. In extreme cases, the display can be a black/white display.

The content of the display according to FIG. 12 essentially corresponds to the display in FIG. 11. In the display in FIG. 12, one of the combination images B' is shown in the evaluation image A. From FIG. 12 it can be particularly seen that also the combination images B' are 2-dimensional and have a plurality of pixels 9.

It can be seen in FIGS. 11 and 12 that other information can also be displayed in the evaluation image A. This other information can, for example, be a first threshold value SW1, a limit time point GZP, GZP', factors F, F' and other values. The significance of these values will become clear later.

In FIGS. 11 and 12 only the part area 18 is shown and output. It is also possible, in addition to the part area 18, to output the complete evaluation image A via the monitor 16 to the user 6. In this case, the part area 18 can be correspondingly marked as in FIG. 7.

In step S39, the evaluation device 8 waits for an input from the user 6. When this input takes place, the evaluation device 8 checks, in step S40, whether the input was a confirmation. If this is the case, the evaluation device 8 creates, in step S41, a report on the basis of the evaluation image A and assigns the evaluation image A and the report to the combination images B'. Then it archives at least the combination images B', the evaluation image A and the report as a unit.

Otherwise, the evaluation device 8 checks, in step S42, whether the input was an instruction to reject the evaluation image A. In this case, the evaluation method is terminated immediately without saving the report.

Otherwise, the computer 8 checks, in step S43, whether the criteria for determining the type and/or the degree of perfusion should be changed. If this is the case, the evaluation device 8 accepts, in step S44, new criteria and returns to step S35.

Even if the criteria are not to be changed, the computer 8, in step S45, accepts a corresponding choice of a pixel 9 or a pixel group. In step S46, the computer 8 determines the time characteristic of the mean value of the corresponding areas of the combination images B' for the selected pixel 9 or the selected pixel group, on the basis of which the computer 8 has determined the degree of perfusion for the selected pixel 9 or the selected pixel group. The pattern is output by the computer 8 in step S47 to the user 6 via the monitor 16.

Figure 6:
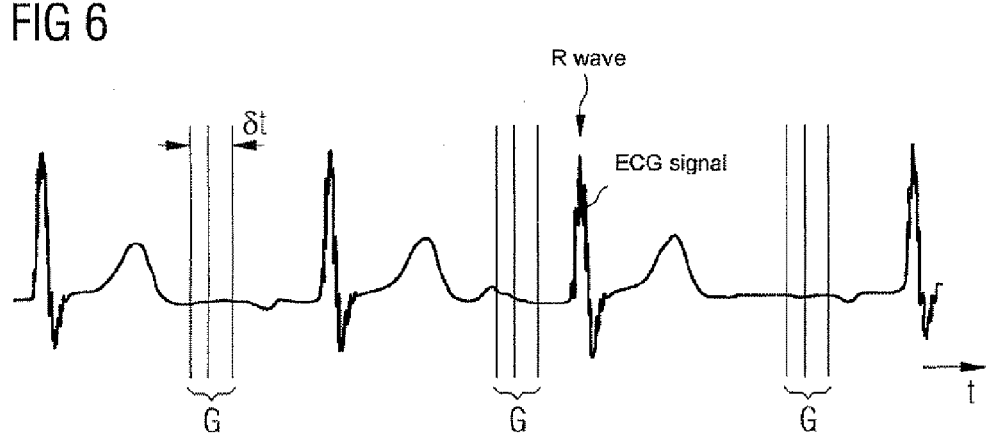
Figure 13:
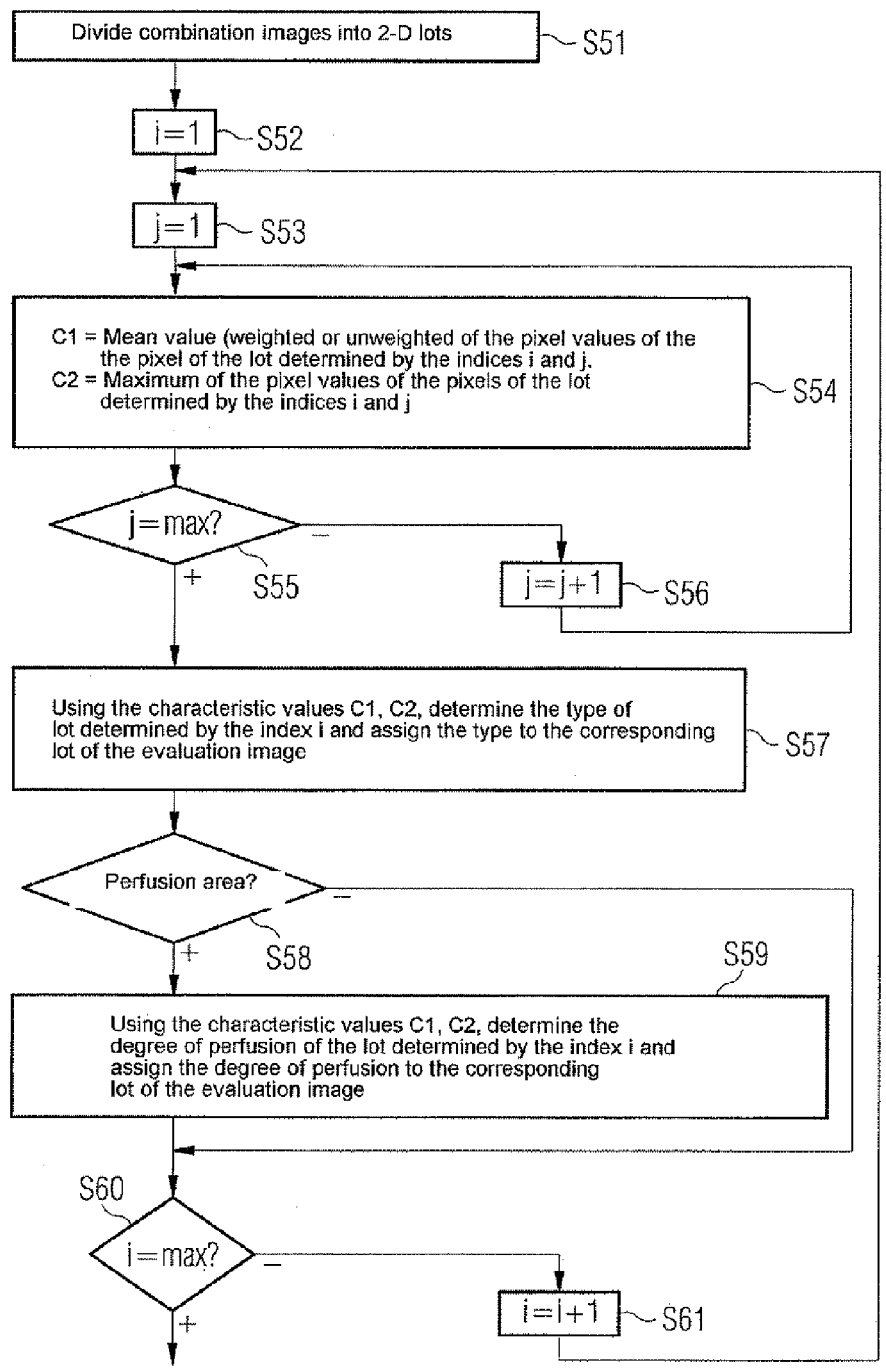

FIG. 13 shows a possible implementation of steps S35 to S37 from FIG. 6.

According to FIG. 13, the computer 8 in step S51, divides the combination images B' into 2-dimensional lots 19. An example of the division of the lots 19 is shown in FIG. 7.

As shown in FIG. 7, the lots 19 are rectangular and are of the same size. This is the simplest way of dividing into lots 19. Other shapes of lot are possible, especially equilateral triangles and regular hexagons. The lots 19 can also be of different sizes, for example smaller in the center of the part area 18 than on the edge of the part area 18. It is also possible to dynamically adapt the lots 19. Possible procedures for this matching are described in the German patent application "Bildauswertungsverfahren für zweidimenionale Projektionsbilder und hiermit korrespondierende Gegenstände" [Image evaluation methods for two-dimensional projection images and objects corresponding herewith] by Siemens A G, Siemens internal file number 200601059, registered at the same time as this invention. This application is mentioned again several times in the following. It is referred to in the following as "application 200601059).

In principle, the size of the lots 19 is optional. They should be 2-dimensional. Furthermore, they should have a sufficient number of pixels 9 to determine the noise trend when averaged and so that any movement artifacts are negligible. The resolution should still be sufficiently good. Tests have shown that the lots 19 should preferably contain between approximately 60 and 1000 pixels 9. For square lots 19, this corresponds to an edge length of 8 to 32 pixels 9.

In steps S52 and S53, a computer 8 sets the run indices i, j to the value one. The index i runs through each lot 19 of the part area 18 in turn. Index j runs through the combination images B' in turn.

In step S54, the evaluation device 8 determines at least one characteristic value C1, C2 for the lot 19 determined by the index i in the combination image B' determined by the index j. In particular, the evaluation device 8 can determine the relevant lot 19 as characteristic values C1, C2 of the, weighted or unweighted, mean value C1 and/or the maximum value C2 of the pixel values of pixels 9.

In step S55, the computer 8 checks whether the index j has reached its maximum value. If this is not the case, the evaluation device 8, in step S56, increments the index j and returns to step S54.

If all the characteristic values C1, C2 for a specific lot 19 have been determined, the evaluation device 8, in step S57, first determines the type of the respective lot 19 on the basis of the characteristic values C1, C2 and assigns the determined type to the corresponding lot 19 of the evaluation image A, see FIG. 11.

In step S58, the evaluation device 8 checks whether it has determined the "perfusion area" type for the relevant lot 19. If this is the case, the evaluation device 8, in step S59, determines the degree of perfusion for this lot 19 on the basis of the characteristic values C11, C2 and likewise assigns it to the corresponding lot 19 of the evaluation image A.

In step S60, the evaluation device 8 checks whether it has already performed steps S53 to S59 for all lots 19. If this is not the case, it increments the index i in step S61 and returns to step S53. Otherwise, the determination and assignment of type and degree of perfusion are terminated.

Various procedures are possible for determining the type and the degree of perfusion. At present, it is preferred to first decide on the basis of the time characteristic of the maximum C2 whether the type "vessel" should be assigned to a specific lot 19. For the lots 19 to which the type "vessel" has not been assigned, the evaluation device 8 decides, in accordance with the present preferred procedure and on the basis of the time pattern of the mean value C1, whether the corresponding lot 19 is of the "background" type or of the "perfusion area" type. The degree of perfusion is preferably determined on the basis of the time characteristic of the mean value C1. Details of this procedure are explained in the following and described in more detail in Application 200601059.

Figure 14:
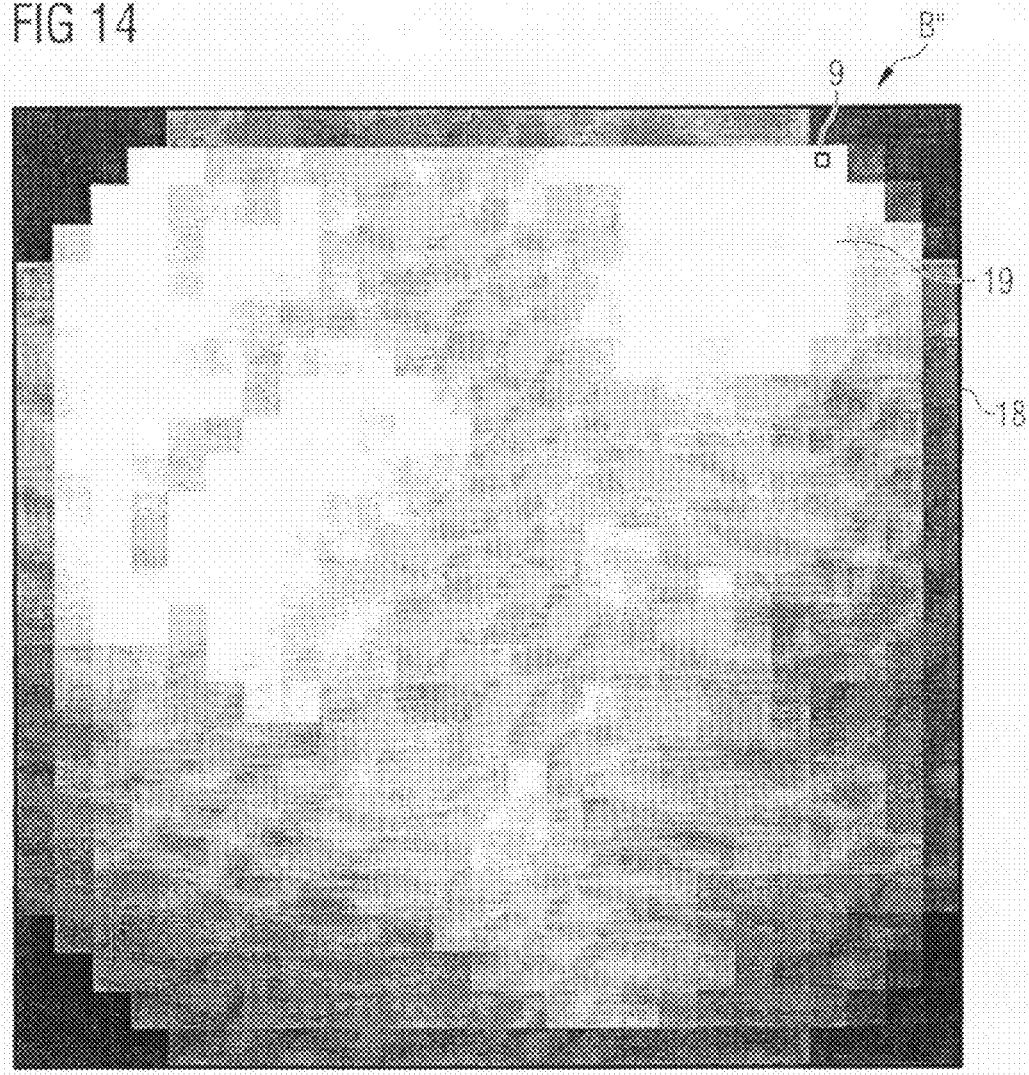

Modifications of the above are, of course, possible in conjunction with the procedure described in FIG. 13. For example, the sequence of the indices i, j can be swapped. In this case, a number of modified combination images B" is determined. Each of these modified combination images B" still only has the characteristic values C1, C2 per lot 19. An example of a projection image B" modified in this way, in which the characteristic value C1 (i.e. the mean value C1) is shown, can be seen in FIG. 14.

The following features especially are realized by the inventive method described above.

The computer 8 undertakes the assignment of the type using the time characteristic of the pixel values of the combination images B'.

The computer 8 undertakes the assignment of the type and of the degree of perfusion using the time characteristic of the pixel values of those pixels 9 of the combination images B' that lie in a 2-dimensional evaluation core 19 of the combination images B' defined by the respective pixel 9 of the evaluation image A. In the context of the inventive method, the evaluation core 19 corresponds to the respective lot 19.

The computer 8 undertakes the uniform assignment of the type and degree of perfusion for all pixels 9 of a lot 19.

The same lots 19 are used to determine the type and to determine the degree of perfusion.

FIGS. 11 and 12 show examples of the result of the assignment.

As an alternative to the assignment of the type and degree of perfusion of the individual pixels 9 of the evaluation image A by lot, it is possible for the computer 8 to determine an own 2-dimensional evaluation core in the combination images B' for each pixel 9 of the evaluation image A. The respective pixel 9 of the evaluation image A in this case corresponds preferably to the centre of gravity of the particular evaluation core. Also in this case, a completely analogous procedure is possible. However, a substantially greater computer effort is required to realize this procedure than for the formation of lots 19. The achievable gain is on the contrary negligible.

For digital images, the zero pixel value is usually assigned to the grey value black and the grey value white is assigned to the maximum possible pixel value (e.g. $2^8-1=255$). Intermediate values are assigned to corresponding grey stages. In the following, the grey value white is assigned to the pixel value zero contrary to the conventional procedure and the grey value black is assigned to the maximum possible pixel value. The intermediate values are assigned correspondingly. This assignment facilitates the understanding of the following explanations. It is, however, not required in principle.

Figure 15:
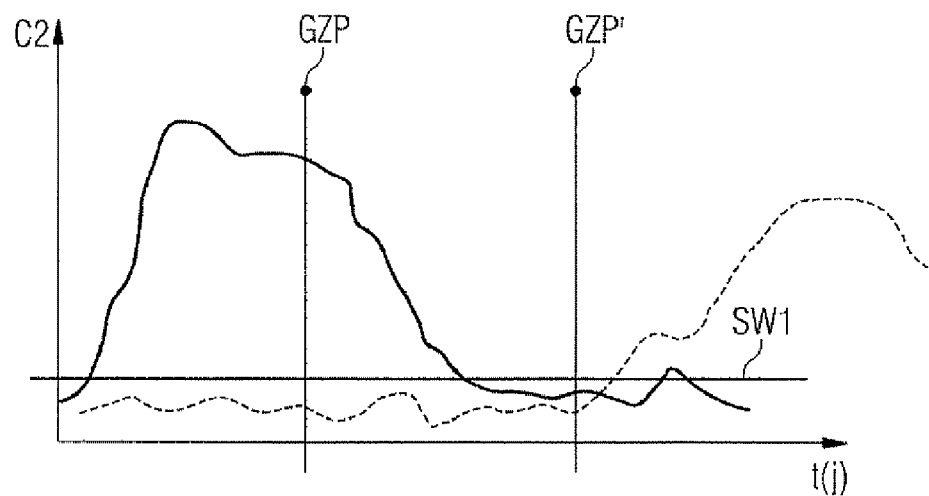
Figure 16:
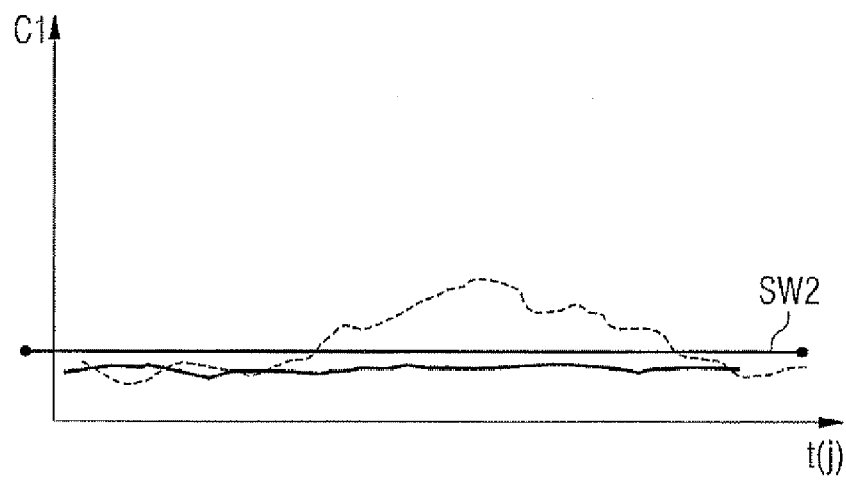

The determination of the type of individual lots 19 by the evaluation device 8 is again described in conjunction with FIGS. 15 and 16.

For the assignment of the "vessel" type, the evaluation device 8 requires three decision criteria, i.e. the first threshold value SW1 and the limit time points GZP, GZP'.

If at a specific lot 19 one of the characteristic values C1, C2 (preferably maximum C2) exceeds the first threshold value SW1, the relevant lot 19 can be assigned the "vessel" type. The "vessel" type is assigned particularly if
  either the first threshold value SW1 is initially exceeded before the first limit time point GZP
  or the first threshold value SW1 is initially exceeded after the second limit time point GZP'.

If necessary, the threshold value for the second limit time point GZP' can also be set somewhat lower than the threshold value SW1 for the first limit time point GZP.

In the first named case, it is assumed that an artery is present in the relevant lot 19; the presence of a vein is assumed in the second case. FIG. 15 shows typical time characteristics for the relevant characteristic value C1, C2 in the case of an artery (pattern shown by a continuous line) and in the case of a vein (pattern shown dotted).

The first threshold value SW1 can be permanently defined. It can, for example, amount to 5 or 10% of the maximum control range. Alternatively, it can be defined relative to the evaluated characteristic value C1, C2 of the particular lots 19 of the combination image B' that occurs first in time. For example, it can amount to 10 or 20% of the corresponding characteristic value C1, C2. Preferably, the first threshold value SW1 depends both on the input by the user 6 and on the corresponding characteristic value C1, C2 of the corresponding lot 19 of the combination image B' that occurs first in time. This can be particularly realized in that the user 6 specifies the factor F of the evaluation device 8 in accordance with step S71 of FIG. 17 and the evaluation device 8 in step S72, determines the first threshold value SW1 for the respective lot 19 as a product of the factor F and of the corresponding characteristic value C1, C2 of the respective lot 19. If a further factor F' is specified, the threshold value for the second limit time point GZP' can be determined by means of the factor F'.

If the "vessel" type is not assigned a lot 19, either the "perfusion area" type or "background" type must be assigned to the lot 19. This distinction also takes place using the time characteristic of the characteristic values C1, C2. Preferably, this distinction can take place on the basis of the mean value C1. For example, a second threshold value SW2 can be defined analogous to the first threshold value SW1. If the time characteristic of the characteristic value C1, C2 under consideration definitely does not exceed the second threshold value SW2, the "background" type is assigned to the relevant lot 19. Otherwise, the "perfusion area" is assigned to the relevant lot 19. FIG. 16 shows an example of a time characteristic for a "background" type of lot 19 (continuous line) and also of a "perfusion area" type of lot 19 (broken line).

The limit time points GZP, GZP' can also be permanently assigned to the computer 8. Preferably, they depend on corresponding inputs by the user 6. Steps S73 and S74 in accordance with FIG. 17 are available for this purpose. In step S73, the evaluation device 8 accepts the limit time points GZP, GZP' from the user 6. In step S74, the evaluation device 8 determines those of the combination images B' that lie nearest in time to the limit time points GZP, GZP'. The evaluation device 8 outputs these combination images B' in the context of step S74, e.g. concurrently, via the monitor 16 to the user 6.

In step S75, the evaluation device 8 checks whether the user 6 confirms the factor F and the limit time point GZP, GZP', or whether he requires a new specification. Accordingly, the evaluation unit 8 either returns to step S71 or continues the process with a step S76 in that the type and extent assignment for the individual lots 19 takes place. The type and extent assignment preferably takes place corresponding to the previously described procedure.

The type and degree of perfusion can be determined in many ways. Some examples are described in the German patent application 10 2005 039 189.3 already mentioned. Further examples can, in particular, be found in application 200601059, which has also already been mentioned.

The presently preferred procedure for determining the degree of perfusion is explained in more detail in the following in conjunction with FIG. 18. In this context, it should be mentioned in advance that in the simplest case only two or three different values are distinguished for the degree of perfusion, i.e. only the values "high" and "low" or "high", "medium" and "low". However, finer distinctions are also possible.

According to FIG. 18, the evaluation device 8 determines a clock rate T1 and clock rate T2. Clock rate T1 is characteristic of the time duration of the rise of the characteristic value C1, C2 under consideration. Clock rate T2 is characteristic of the time duration of the fall of the characteristic value C1, C2 under consideration. The degree of perfusion is determined using the quotient of the two clock rates T1, T2. If, for example, the quotient is below a lower boundary US, a perfusion degree 1 is detected. If the quotient is above an upper boundary OS, a perfusion degree 3 is detected. If the quotient is between the two boundaries US, OS, a perfusion degree 2 is detected.

Variations of this procedure are, of course, also possible.

The inventive evaluation method described above can be refined as necessary. For example, it is possible to carry out a finer determination after the lotwise determination of the degree of perfusion, i.e. for example to divide the relevant lots 19. Alternatively, it is possible to combine several lots 19 to whom the "perfusion area" type is assigned, before the degree of perfusion is determined, in order to reduce the computing effort. Such possible refinements are particularly explained in Application 200601059. Procedures for detecting outliers are also possible.

It was assumed in the above explanations that the relevant recording parameters of the recording arrangement, including the operating parameters of the x-ray source 4 could always be set the same when capturing the images B. If this precondition is not met, fluctuations in brightness in the captured image B can occur which could impair the evaluation or in extreme cases even make it impossible. In the context of this present invention it is therefore provided for all the relevant corrections to be undertaken as necessary. These corrections take place before step S35 or after step S44 of FIG. 6. They are explained in more detail in the following in conjunction with FIG. 19.

According to FIG. 19, in step S81, a reference area 20 of the combination image B' is first determined. In the simplest case, the determination of the reference area 20 takes place by means of a suitable user input. In step S82, the evaluation device 8 preferably displays the reference area 20 in one of the combination images B', in one of the projection images B or in the evaluation image A. An example of this is shown in FIG. 7.

In step S83, the evaluation device 8 specifies one of the combination images B' as a reference image. Which of the combination images B' is specified as the reference image is, in principle, arbitrary. As a rule, the first or last of the combination images B' is specified as a reference image.

In step S84, the evaluation device 8 selects one of the combination images B. In step S85 the evaluation device 8 compares the selected combination image B' with the reference image. The comparison takes place only within reference areas 20 that correspond to each other. Using the comparison, the evaluation device 8, in step S86, determines a transformation of the pixel values of the selected combination image B'. The transformation is determined in such a way that the mean value of the pixels 9 of the reference area 20 of the transformed combination image B' on one hand and the mean value of the pixels 9 of the reference area 20 of the reference image on the other hand are in a predetermined functional relationship to each other. The functional relationship can especially exist in that the mean value of the pixels 9 of the reference area 20 of the transformed combination image B' is the same as the mean value of the pixels 9 of the reference image. The transformation can be either linear or non-linear.

Corresponding to the transformation determined in step S86, the evaluation device 8 transforms, in step S87, all pixels 9 of the selected combination image B'. i.e. both the pixels 9 within the reference area 20 and also the pixels 9 outside the reference area 20.

In step S88, the evaluation device 8 checks whether it has already performed steps S84 to S87 for all the combination images B'. If this is not the case, it goes to step S89 in that it selects a different one of the combination images B'. It then returns to step S85, otherwise the transformation of the combination images B' is terminated.

As an alternative to a specification of the reference area 20 by the user 6, it is possible for the evaluation device 8 to automatically determine the reference area 20. For example, the evaluation device 8 can determine the reference area 20 using the pixels 9 of the evaluation image A to which it has assigned the "background" type. Lots 19 that lie outside the exposure area are not considered in this case. Realizations for detecting lots 19 that lie outside the exposure area are generally known.

If the evaluation device 8 automatically determines the reference area 20, it is possible, as an alternative or addition to the procedure in FIG. 19, to also take account of information on the recording geometry and/or the injection point of the contrast medium. In this case, the evaluation device 8 calls up relevant information and takes it into account when choosing the lots 19 of the reference area 20.

It is possible to output the reference area 20 corresponding to FIG. 7 to the user 6 via the monitor 16. This places the user 6 in a position to check the reference area 20, to confirm it, reject it or change it as necessary.

If the capture of the images B takes place when the object under examination 3 (i.e. usually a human 3) is holding his breath, the procedure described above guarantees that the object under examination 3 is essentially always arranged in the same area in the combination images B'. However, it is also conceivable for a macroscopic movement to be superimposed on the intrinsic movement of the object under examination 3. In particular, respiration can take place. In this case the evaluation method can be even further optimized.

Position correction is not necessary with regard to the positions of the projection images B of the individual groups G relative to each other. This is because the type of capture guarantees that with respect to each group G the object under examination 3 is mapped in essentially the same position in the projection images B of the respective group G. It is, however, possible that the position of the object under examination 3 in the projection images B (and therefore also in the combination images B') varies from group G to group G. According to FIG. 20, it can therefore be appropriate to insert steps S91 and S92 between steps S34 and S35 of FIG. 6.

In step S91, the computer 8 determines the position of the object under examination 3 in the combination images B'. For example, the computer 8 can determine the position of the diaphragm and/or ribs in one of the projection images B of the respective group G. Alternatively or additionally, the computer 8 can determine the position of the previously-known positions of the vascular system in one of the projection images B or in the combination image B' of the respective group G. For example, a search can be made for known branches. In this case, the computer 8 determines the position of the object under examination 3 in the projection images B and in the combination image B' for each group G by using at least one of the projection images B or the combination image B' of the respective group G.

It is possible as an alternative or addition for additional information that is not contained as such in the projection images B to be assigned to the groups G. This additional information corresponds in this case to the position of the object under examination 3 in the projection images B. For example, when acquiring images by means of the control device 2, the respiratory state of the patient 3 can be detected by using an elastic pectoral girdle or some other suitable sensor, and assigned to the projection images B of the respective group G. In this case, the computer 8 can, by using the additional information, determine the position of the object under examination 3 in the projection images B and/or in the combination image B' for each group G.

In step S92, the computer 8 registers the combination images B' relative to each other. For example, it can leave one of the combination images B' unchanged and rotate and/or shift the other combination images B' relative to this aforementioned combination image B'. The extent of the rotation and/or shift to be made is obtained from the determined positions of the combination images B'. Elastic image shifts are also possible as an alternative to a rotation and/or shift of the complete combination images B' which is uniform for the respective combination image B'. Elastic image shifts as such are known and therefore need not be explained further in the following.

The inventive evaluation method represents substantial progress compared to the evaluation methods according to prior art. Especially, with the evaluation methods according to the invention it is not necessary to define an ROI (region of interest). Furthermore, it is not necessary to define which part of the combination images B' are "vessels", "perfused part of the environment" or "non-perfused part of the environment". This definition is, on the contrary, performed by the evaluation unit 8 itself. Image warping is then only necessary if the projection images B were not captured during a respiration holding phase.

The evaluation method according to the invention has a high degree of automation and a high processing speed. Furthermore, it is very flexible, including with respect to the visualization of the evaluation results and interactivity. Finally, it is possible to integrate the evaluation method according to the invention into a "TIMI flow measurement". A duplicate capture of the projection images B in conjunction with a resulting duplicate x-ray exposure of the patient 3 is therefore no longer necessary.

The above description serves exclusively to explain this present invention. The scope of protection of this present invention should, however, be exclusively defined by the accompanying claims.

The invention claimed is:

1. A method for evaluating a group of projection images of an object under examination, comprising:
    defining combination images having a plurality of pixels with pixel values based on the projection images in the group, a sequence of the combination images indicating a time characteristic of the pixel values showing a distribution of a contrast medium over time in the object;
    determining an evaluation image having a plurality of pixels with pixel values based on the combination images, the pixels of the evaluation image corresponding to the pixels of the combination images;
    assigning a type to each pixel in an area of the evaluation image corresponding to a type selected from the group consisting of: a vessel of the object, a perfusion area of the object, and a background of the object; and performing the type assignment based on the time characteristic of the pixel values of the combination images for identifying a vascular system of the object,
    wherein the object is an iteratively moving object,
    wherein the combination images are selected from a series of projection images of the iteratively moving object each having an assigned phase information that deviates by a maximum of one phase boundary from a reference phase,
    wherein the reference phase or the phase boundary is specified by a user, and
    wherein a number of the selected combination images is determined and outputted to the user.

2. The method as claimed in claim 1, wherein the pixel values of the pixels are defined in at least essentially identical areas of the object in the projection images.

3. The method as claimed in claim 1, wherein one of the projection images is selected by the user and outputted together with the assigned phase information or the deviation of the assigned phase information to the user.

4. The method as claimed in claim 1,
    wherein a type evaluation core is defined by pixels of an evaluation image, and
    wherein the type assignment is performed to pixels of the combination images that are in the type evaluation core based on a time characteristic of pixel values of the pixels.

5. The method as claimed in claim 4, wherein the type assignment is performed by:
    type lots that are divided in an area of the evaluation image, or
    a time characteristic of a weighted or unweighted mean value or a maximum of pixel values of the pixels occurring in the type evaluation core.

6. The method as claimed in claim 5, wherein the type evaluation core corresponds to the type lots.

7. The method as claimed in claim 4, wherein one of the projection or combination images is displayed in the evaluation image.

8. The method as claimed in claim 4,
    wherein a degree of perfusion for pixels of the perfusion area in the evaluation image is determined and assigned to the pixels,
    wherein an extent evaluation core is defined by the pixel of the evaluation image, and
    wherein the assignment of the degree of perfusion is performed to pixels of the combination images that are in the extent evaluation core based on a time characteristic of pixel values of the pixels.

9. The method as claimed in claim 8, wherein the assignment of the degree of perfusion is performed by:
    extent lots that are divided in an area of the evaluation image, or
    a time characteristic of a weighted or unweighted mean value of pixel values of the pixels occurring in the extent evaluation core.

10. The method as claimed in claim 9, wherein the extent evaluation core corresponds to the extent lots.

11. The method as claimed in claim 8, wherein the extent evaluation core is identical to the type evaluation core.

12. The method as claimed in claim 8, wherein the degree of perfusion of the perfusion area of the evaluation image is converted into a color value using an assignment rule and the perfusion area of the evaluation image is outputted to the user with a corresponding color-coded display.

13. The method as claimed in claim 12, wherein the assignment rule is outputted to the user together with the color-coded display.

14. The method as claimed in claim 4, further comprising:
specifying one of the combination images as a reference image,
comparing a reference area of each combination image with a corresponding reference area of the reference image,
determining a transformation of pixel values based on the comparison so that a mean value of the pixel values of the reference area of the each combination image is a function of a mean value of the pixel values of the corresponding reference area of the reference image, the function being predetermined, and
transforming the pixel values of the each combination image based on the transformation.

15. The method as claimed in claim 14, wherein the reference area is displayed in the evaluation image or in one of the projection or combination images.

16. The method as claimed in claim 1,
wherein a position of the object in the group of the projection images is at least essentially identical and determined in the combination images, and
wherein the combination images are registered relative to each other.

17. The method as claimed in claim 16, wherein the position is determined using:
one of the projection or combination images in the group, or
additional information assigned to the group corresponding to the position that is not contained in the projection images.

18. A non transitory computer readable medium storing a computer program for performing a method for evaluating a group of projection images of an object under examination, comprising:
a computer subroutine that is configured to:
define combination images having a plurality of pixels with pixel values based on the projection images in the group, a sequence of the combination images indicating a time characteristic of the pixel values showing a distribution of a contrast medium over time in the object,
determine an evaluation image having a plurality of pixels with pixel values based on the combination images, the pixels of the evaluation image corresponding to the pixels of the combination images,
assign a type to each pixel in an area of the evaluation image corresponding to a type selected from the group consisting of: a vessel of the object, a perfusion area of the object, and a background of the object, and
perform the type assignment based on the time characteristic of the pixel values of the combination images for identifying a vascular system of the object,
wherein the object is an iteratively moving object,
wherein the combination images are selected from a series of projection images of the iteratively moving object each having an assigned phase information that deviates by a maximum of one phase boundary from a reference phase,
wherein the reference phase or the phase boundary is specified by a user, and
wherein a number of the selected combination images is determined and outputted to the user.

19. A medical device for evaluating a group of projection images of an object under examination, comprising:
an image recording device that records the projection images of the object; and
a computer that:
defines combination images having a plurality of pixels with pixel values based on the projection images in the group, a sequence of the combination images indicating a time characteristic of the pixel values showing a distribution of a contrast medium over time in the object,
determines an evaluation image having a plurality of pixels with pixel values based on the combination images, the pixels of the evaluation image corresponding to the pixels of the combination images,
assigns a type to each pixel in an area of the evaluation image corresponding to a type selected from the group consisting of: a vessel of the object, a perfusion area of the object, and a background of the object, and
performs the type assignment based on the time characteristic of the pixel values of the combination images for identifying a vascular system of the object,
wherein the object is an iteratively moving object,
wherein the combination images are selected from a series of projection images of the iteratively moving object each having an assigned phase information that deviates by a maximum of one phase boundary from a reference phase,
wherein the reference phase or the phase boundary is specified by a user, and
wherein a number of the selected combination images is determined and outputted to the user.

* * * * *